US009241652B2

(12) United States Patent
Adachi et al.

(10) Patent No.: US 9,241,652 B2
(45) Date of Patent: Jan. 26, 2016

(54) AUDITORY EVENT-RELATED POTENTIAL MEASUREMENT SYSTEM, AUDITORY EVENT-RELATED POTENTIAL MEASUREMENT METHOD, AND COMPUTER PROGRAM THEREOF

(71) Applicant: Panasonic Corporation, Osaka (JP)

(72) Inventors: Shinobu Adachi, Nara (JP); Jun Ozawa, Nara (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 428 days.

(21) Appl. No.: 13/938,274

(22) Filed: Jul. 10, 2013

(65) Prior Publication Data

US 2013/0296732 A1  Nov. 7, 2013

Related U.S. Application Data

(63) Continuation of application No. PCT/JP2012/006616, filed on Oct. 16, 2012.

(30) Foreign Application Priority Data

Oct. 19, 2011 (JP) ................................. 2011-229357

(51) Int. Cl.
*A61B 5/04* (2006.01)
*A61B 5/0484* (2006.01)
(Continued)

(52) U.S. Cl.
CPC ......... *A61B 5/04845* (2013.01); *A61B 5/04842* (2013.01); *A61B 5/125* (2013.01); *A61B 5/6803* (2013.01)

(58) Field of Classification Search
CPC .................... A61B 5/04842; A61B 5/04845
See application file for complete search history.

(56) References Cited

U.S. PATENT DOCUMENTS 5,549,118 A * 8/1996 John ................... A61B 5/04845
                                                        600/554
7,593,767 B1 * 9/2009 Modarres ............... A61B 5/048
                                                        600/529
(Continued)

FOREIGN PATENT DOCUMENTS

CN    2753290 Y    1/2006
CN    100462055 C    2/2009
(Continued)

OTHER PUBLICATIONS

Hoppe, U., et al., "Loudness perception and late auditory evoked potentials in adult cochlear implant users", 2001.
(Continued)

*Primary Examiner* — Etsub Berhanu
*Assistant Examiner* — Angeline Premraj
(74) *Attorney, Agent, or Firm* — Renner, Otto, Boisselle & Sklar, LLP

(57) ABSTRACT

An auditory event-related potential measurement system includes: a video output section configured to present a video to a user; a measurement section configured to measure a user's electroencephalogram signal; a scheduling section configured to schedule a timing of presenting an auditory stimulation so that the auditory stimulation is presented during a period in which the video is being presented to the user; an auditory stimulation output section configured to present the auditory stimulation to the user at the scheduled timing; and a processing section configured to acquire, from the electroencephalogram signal, an event-related potential in a first time range as reckoned from a point in time at which the auditory stimulation is presented. When an amount of video luminance change exceeds a threshold value, the auditory stimulation is not presented during a second time range as reckoned from a point in time at which the threshold value is exceeded.

14 Claims, 12 Drawing Sheets

(51) Int. Cl.
*A61B 5/12* (2006.01)
*A61B 5/00* (2006.01)

(56) References Cited

U.S. PATENT DOCUMENTS

| | | |
|---|---|---|
| 2003/0125634 A1 | 7/2003 | Eda et al. |
| 2007/0083097 A1 | 4/2007 | Fujiwara et al. |
| 2009/0247895 A1 | 10/2009 | Morikawa et al. |
| 2011/0071828 A1 | 3/2011 | Adachi et al. |

FOREIGN PATENT DOCUMENTS

| | | |
|---|---|---|
| CN | 101589358 A | 11/2009 |
| CN | 102112051 A | 6/2011 |
| EP | 1 316 288 A2 | 6/2003 |
| JP | 07-313494 A | 12/1995 |
| JP | 2003-159253 A | 6/2003 |
| JP | 2006-187305 A | 7/2006 |
| JP | 2009-268826 A | 11/2009 |

OTHER PUBLICATIONS

Mariam, M., et al., "Comparing the habituation of late auditory evoked potentials to loud and soft sound", 2009.
Sato et al., "Basic and Clinical Evoked Potential", p. 129, Sozo-Shuppan, 1990 (first edition) and concise explanation.
"Shin Seirishinrigaku" (or "New Physiopsychology"), supervised by Miyata (third edition), vol. 1, p. 115, 1998 and concise explanation.
Naatanen, R, "Attention and brain function", p. 126, 1992 and concise explanation.
International Search Report for corresponding International Application No. PCT/JP2012/006616 mailed Nov. 20, 2012.
Chinese Search Report for corresponding International Application No. 201280003419.1 dated May 12, 2015 (with English translation).

\* cited by examiner

*FIG. 7A*

| TIMINGS OF LUMINANCE CHANGE (ms) |
| --- |
| 1542 |
| 2210 |
| 2479 |
| 2776 |
| 8412 |
| 15337 |
| 21492 |
| 22521 |
| 23184 |
| 29173 |
| ... |

*FIG. 7B*

| INITIAL SCHEDULE (ms) | CHANGED SCHEDULE ACCORDING TO TIMINGS OF LUMINANCE CHANGE | |
| --- | --- | --- |
| | Case1: SKIPPING (ms) | Case2: CORRECTION (ms) |
| 271 | 271 | 271 |
| 605 | 605 | 605 |
| 888 | 888 | 888 |
| 1234 | 1234 | 1234 |
| 1513 | | 1743 |
| 1778 | 1778 | 2008 |
| 2115 | | 2977 |
| 2423 | | 3285 |
| 2745 | | 3607 |
| 2966 | | 3828 |
| 3299 | 3299 | 4161 |
| 3578 | 3578 | 4440 |
| 3906 | 3906 | 4767 |
| 4210 | 4210 | 5072 |
| ... | ... | ... |

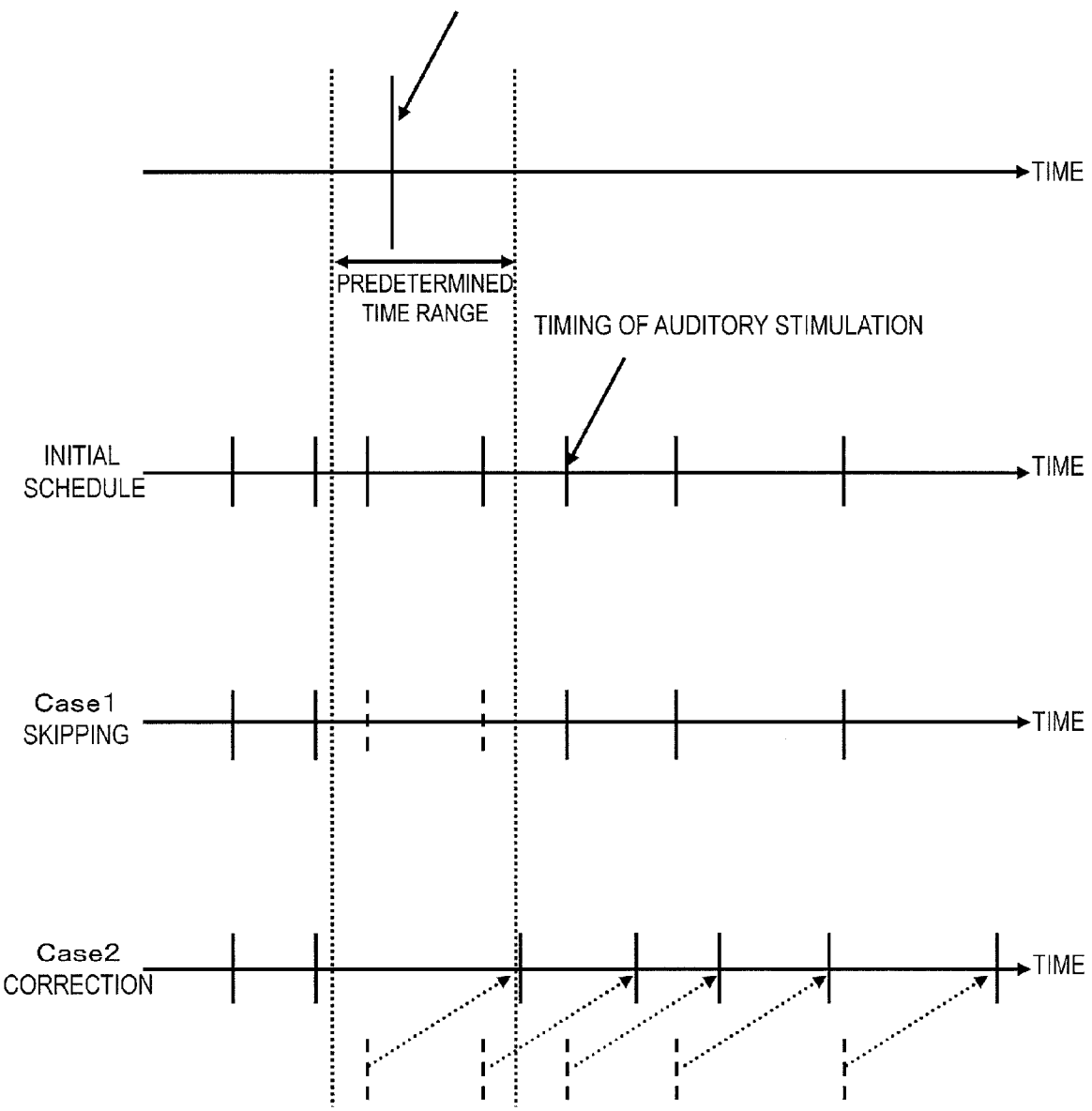

*FIG.9*
| TRIAL NUMBER | AUDITORY STIMULATION INFORMATION | | | IGNORABLE TRIAL FLAG | EVENT-RELATED POTENTIAL |
|---|---|---|---|---|---|
| | RIGHT/LEFT | FREQUENCY (Hz) | SOUND PRESSURE (dB HL) | | |
| 1 | 1 | 1000 | 70 | 0 |  |
| 2 | 2 | 2000 | 80 | 0 |  |
| 3 | 2 | 500 | 75 | 0 |  |
| 4 | 1 | 4000 | 80 | 1 | 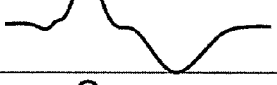 |
| 5 | 1 | 2000 | 70 | 0 | 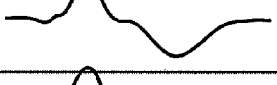 |
| 6 | 1 | 1000 | 75 | 0 |  |
| 7 | 2 | 4000 | 80 | 1 | 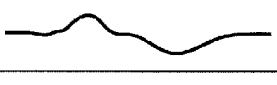 |
| 8 | 1 | 500 | 70 | 1 | 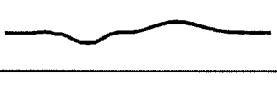 |
| 9 | 2 | 2000 | 80 | 0 |  |
| 10 | 2 | 500 | 75 | 0 | 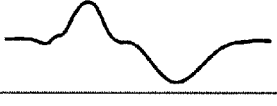 |
| ... | ... | ... | ... | ... | ... |
INFORMATION RECEIVED FROM AUDITORY STIMULATION GENERATION SECTION 60
INFORMATION RECEIVED FROM IGNORABLE TRIAL DETERMINATION SECTION 80
INFORMATION RECEIVED FROM ELECTROENCEPHALOGRAM PROCESSING SECTION 55

AUDITORY EVENT-RELATED POTENTIAL MEASUREMENT SYSTEM, AUDITORY EVENT-RELATED POTENTIAL MEASUREMENT METHOD, AND COMPUTER PROGRAM THEREOF

This is a continuation of International Application No. PCT/JP2012/006616, with an international filing date of Oct. 16, 2012, which claims priority of Japanese Patent Application No. 2011-229357, filed on Oct. 19, 2011, the contents of which are hereby incorporated by reference.

TECHNICAL FIELD

The present disclosure relates to a technique of measuring with a high accuracy an auditory event-related potential in response to an auditory stimulation. More specifically, the present disclosure relates to a method of presenting an auditory stimulation while presenting a video, and measuring an auditory event-related potential without being influenced by fluctuations in the arousal level of a user or the video.

DESCRIPTION OF THE RELATED ART

In recent years, due to the downsizing and improved performance of hearing aids, there is an increasing number of users of hearing aids. In accordance with the deteriorated state of hearing of each user, a hearing aid amplifies an audio signal of a frequency band in which his or her hearing has deteriorated, this amplification being adapted to the degree of hearing deterioration. This makes it easier for the user to hear sounds.

Since each user may have a different deteriorated state of hearing, it is necessary to correctly evaluate each user's hearing before beginning the use of a hearing aid. Then, based on that evaluation result, a "fitting" is performed to determine an amount of sound amplification for each frequency.

Generally speaking, hearing of each user is evaluated based on the user's subjective report. However, evaluation through subjective reporting has problems in that the results will vary depending on the linguistic expression and personality, and that evaluation is impossible with infants who are unable to give subjective reports. Therefore, techniques of objectively evaluating hearing without relying on any subjective reporting are under development.

An electroencephalogram is an effective tool for measuring user states such as perception and cognition. An electroencephalogram, which reflects neural activities of the cerebral cortex, is obtained by recording potential changes between two points on the scalp. While recording an electroencephalogram through electrodes which are worn on the scalp of a user, an auditory stimulation is presented to the user, in response to which a characteristic electroencephalogram is induced based on the auditory stimulation as a starting point. This electroencephalogram is called an auditory event-related potential. An auditory event-related potential is an index which enables objective evaluation of a user's hearing. An auditory event-related potential contains an extrinsic component (auditory evoked potential) which is evoked by an auditory stimulation, as well as an intrinsic component caused by exposure to the auditory stimulation.

Hoppe, U., et al., "Loudness perception and late auditory evoked potentials in adult cochlear implant users", 2001 (hereinafter referred to as "Non-Patent Document 1") suggests a possibility of being able to identify a relationship between "loudness" (as a user's subjective index of perceived loudness) and the amplitude and latency of an N1 component in response to an auditory stimulation of a pure tone, and estimate a loudness, among other hearing evaluations, from the amplitude and latency of the N1 component. Note that an "N1 component" is a negative sensory evoked potential which is induced at about 100 ms based on the presentation of an auditory stimulation as a starting point. Since the N1 component reflects neural activities of the cerebral cortex, it is believed that the N1 component has a higher correlation with one's subjective perception than a brain stem response (ABR) does. This indicates a possibility that loudness, among other hearing evaluations, can be estimated from the amplitude and latency of the N1 component.

Mariam, M., et al., "Comparing the habituation of late auditory evoked potentials to loud and soft sound", 2009 (hereinafter referred to as "Non-Patent Document 2") discloses an uncomfortableness level estimation technique utilizing habituation of the N1 component. An "uncomfortableness level" (uncomfortable level: also referred to as "UCL" in the present specification) is a smallest sound pressure that is too loud to be heard for a long time. This technique utilizes the fact that habituation of the N1 component does not occur when a sound is so loud that it is unignorable.

Since an auditory event-related potential has a low signal-to-noise ratio (S/N) relative to the background electroencephalogram, it is necessary to reduce the influence of mixed noises by repetitively presenting the stimulation and taking an arithmetic mean. Therefore, given a number N of repetitions, an amount of time which is equal to N times the stimulation interval is needed. For example, in Non-Patent Document 2, where 800 times of repetition are made with a stimulation interval of 1 second, 800 seconds (i.e., ten and several minutes) are required for each kind of auditory stimulation.

SUMMARY

In the aforementioned conventional techniques, there is a need to conduct quicker electroencephalogram measurement, and make more accurate hearing evaluations.

A non-limiting and illustrative embodiment of the present disclosure provides, in an auditory event-related potential measurement system for hearing evaluation, a technique of suppressing fluctuations in auditory event-related potential due to changes in the arousal level, and measuring an auditory event-related potential with a high accuracy.

In one general aspect, an auditory event-related potential measurement system disclosed herein includes: a video output section configured to present a video to a user; a biological signal measurement section configured to measure an electroencephalogram signal of the user; an auditory stimulation scheduling section configured to schedule a timing of presenting an auditory stimulation so that the auditory stimulation is presented during a period in which the video is being presented to the user; an auditory stimulation output section configured to present the auditory stimulation to the user at the scheduled timing; and an electroencephalogram processing section configured to acquire, from the electroencephalogram signal, an event-related potential in a first time range as reckoned from a point in time at which the auditory stimulation is presented, wherein the auditory stimulation scheduling section schedules the timing of presenting the auditory stimulation so that, when an amount of luminance change in the output video exceeds a predetermined threshold value, the auditory stimulation is not presented during a second time range as reckoned from a point in time at which the predetermined threshold value is exceeded.

According to the above aspect, fluctuations in auditory event-related potential due to noises associated with changes in the arousal level of a user and the user's watching a video are reduced, whereby a highly accurate auditory event-related potential measurement can be realized.

These general and specific aspects may be implemented using a system, a method, and a computer program, or any combination of systems, methods, and computer programs.

Additional benefits and advantages of the disclosed embodiments will be apparent from the specification and Figures. The benefits and/or advantages may be individually provided by the various embodiments and features of the specification and drawings disclosure, and need not all be provided in order to obtain one or more of the same.

BRIEF DESCRIPTION OF THE DRAWINGS

FIGS. 7A and 7B are diagrams showing example timings of luminance change received by an auditory stimulation scheduling section 65 and schedule changes for auditory stimulations made by the auditory stimulation scheduling section 65.

FIG. 8 is a diagram illustrating the notion of schedule changes for auditory stimulations.

FIG. 9 is a diagram showing examples of data retained by an auditory event-related potential calculation section 100.

DETAILED DESCRIPTION

Figure 1A:
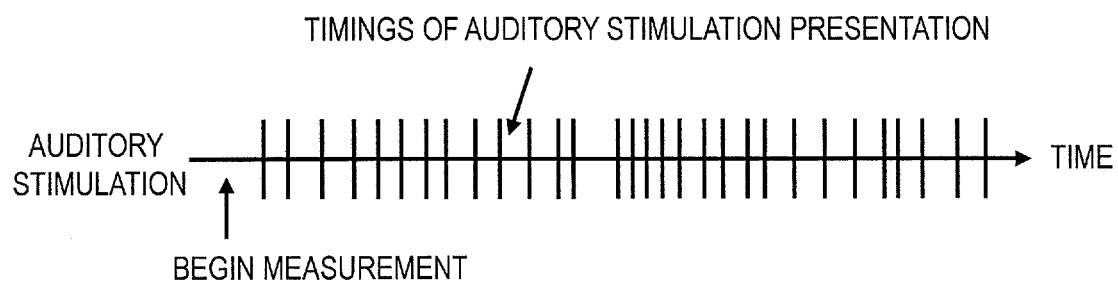
FIGS. 1A and 1B are diagrams showing an auditory event-related potential measurement paradigm where only auditory stimulations are used, and imaginary changes in arousal level during an auditory event-related potential measurement.

In conventional techniques such as Non-Patent Document 1 and Non-Patent Document 2 above, a monotonous auditory stimulation is presented for a long time. For this reason, the user may often be unable to maintain his or her arousal level. As is stated in supervised by Sato et al., "BASIC AND CLINICAL EVOKED POTENTIAL", p. 129, SOZO-SHUPPAN, 1990 (first edition), it is currently believed that the auditory event-related potential undergoes great changes in its waveform depending on the arousal level. Therefore, even when a hearing evaluation is made by the conventional techniques using the amplitude and latency of an N1 component, there is a possibility that the evaluation may not be correct.

Hereinafter, with reference to the attached drawings, embodiments of the auditory event-related potential measurement system according to the present disclosure will be described.

First, the terminology used in the present specification will be described.

An "event-related potential (event-related potential: ERP)" is a kind of electroencephalogram (electroencephalogram: EEG), and refers to a transient potential fluctuation of the brain that occurs in temporal relationship with an external or internal event.

An "auditory event-related potential" is an event-related potential that is induced in response to an auditory stimulation. Examples thereof are: a P1 component, which is a positive potential that is induced at about 50 ms since an auditory stimulation as a starting point; an N1 component, which is a negative potential that is induced at about 100 ms since an auditory stimulation as a starting point; and a P2 component, which is a positive potential that is induced at about 200 ms since an auditory stimulation as a starting point.

To "present an auditory stimulation" means outputting a pure tone, e.g., outputting a pure tone through one ear of headphones.

A "pure tone" is a sound, repeating its periodic oscillation, that is expressed by a sine wave having only one frequency component. The type of headphones for presenting pure tones may be arbitrary, so long as the headphones are able to accurately output a pure tone with a designated sound pressure. This makes it possible to correctly measure an uncomfortable sound pressure.

An auditory event-related potential measurement system according to the present disclosure reduces changes in the arousal level of a user by presenting visual stimulations in the form of a video, in addition to auditory stimulations. Then, an auditory event-related potential which is much less affected by changes in arousal level is measured. Moreover, the timing of presenting auditory stimulations for auditory event-related potential measurement is controlled in accordance with the timings of luminance change in the presented video, thus reducing the influence of noises that are induced by the presented video.

The outline of one implementation of the present disclosure is as follows.

An auditory event-related potential measurement system as one implementation of the present disclosure includes: a video output section configured to present a video to a user; a biological signal measurement section configured to measure an electroencephalogram signal of the user; an auditory stimulation scheduling section configured to schedule a timing of presenting an auditory stimulation so that the auditory stimulation is presented during a period in which the video is being presented to the user; an auditory stimulation output section configured to present the auditory stimulation to the user at the scheduled timing; and an electroencephalogram processing section configured to acquire, from the electroencephalogram signal, an event-related potential in a first time range as reckoned from a point in time at which the auditory stimulation is presented. The auditory stimulation scheduling section schedules the timing of presenting the auditory stimulation so that, when an amount of luminance change in the output video exceeds a predetermined threshold value, the auditory stimulation is not presented during a second time range as reckoned from a point in time at which the predetermined threshold value is exceeded.

In one embodiment, the auditory event-related potential measurement system further includes a calculation section configured to take an arithmetic mean of the event-related potential acquired by the electroencephalogram processing section. The auditory stimulation output section presents a plurality of auditory stimulations including a first auditory stimulation and a second auditory stimulation, the second auditory stimulation being presented next to the first auditory stimulation; and if the second auditory stimulation is presented at a time interval which is predetermined or longer from the first auditory stimulation, the calculation section takes an arithmetic mean of event-related potentials which are evoked by those auditory stimulations among the plurality of auditory stimulations excluding the second auditory stimulation.

In one embodiment, the first auditory stimulation and the second auditory stimulation presented by the auditory stimulation output section have respectively different frequencies.

In one embodiment, the calculation section takes an arithmetic mean of event-related potentials which are evoked by those auditory stimulations among the plurality of auditory stimulations excluding the second auditory stimulation.

In one embodiment, the auditory stimulation scheduling section schedules the timing of presenting the auditory stimulation by designating as the second time range a range of not less than 50 ms and not more than 200 ms after the point in time at which the amount of luminance change exceeds the predetermined threshold value.

In one embodiment, the auditory event-related potential measurement system further includes a video reproduction processing section configured to retain a video content to be presented to the user, and performing a reproduction process of the retained content. The video output section presents to the user the video content having been subjected to the reproduction process.

In one embodiment, the video content does not contain audio information.

In one embodiment, when the video content contains any audio information, the video output section prohibits outputting of the audio.

In one embodiment, the video reproduction processing section retains a plurality of types of video contents; and the video reproduction processing section performs a reproduction process of a video content selected by the user from among the plurality of types of video contents.

In one embodiment, if the second auditory stimulation is presented at an interval of 2 seconds or more from the first auditory stimulation, the calculation section takes an arithmetic mean of event-related potentials which are evoked by those auditory stimulations among the plurality of auditory stimulations excluding the second auditory stimulation.

In one embodiment, if the second auditory stimulation is presented at an interval of 6 seconds or more from the first auditory stimulation, the calculation section takes an arithmetic mean of event-related potentials which are evoked by those auditory stimulations among the plurality of auditory stimulations excluding the second auditory stimulation.

In one embodiment, the auditory event-related potential measurement system further includes an auditory stimulation generation section configured to determine which of right and left ears of the user the auditory stimulation is to be presented to and determining a frequency and a sound pressure of the auditory stimulation, and generating the auditory stimulation with characteristics so determined.

A method as one implementation of the present disclosure includes the steps of: presenting a video to a user; measuring an electroencephalogram signal of the user; scheduling a timing of presenting an auditory stimulation so that the auditory stimulation is presented during a period in which the video is being presented to the user; presenting the auditory stimulation to the user at the scheduled timing; and from the electroencephalogram signal, acquiring an event-related potential in a first time range as reckoned from a point in time at which the auditory stimulation is presented. The scheduling step schedules the timing of presenting the auditory stimulation so that, when an amount of luminance change in the output video exceeds a predetermined threshold value, the auditory stimulation is not presented during a second time range as reckoned from a point in time at which the predetermined threshold value is exceeded.

A computer program as one implementation of the present disclosure is a computer program stored on a non-transitory computer-readable medium, and to be executed by a computer provided in an auditory event-related potential measurement apparatus of an auditory event-related potential measurement system, the computer program causing the computer to execute the steps of: presenting a video to a user; acquiring an electroencephalogram signal of the user; scheduling a timing of presenting an auditory stimulation so that the auditory stimulation is presented during a period in which the video is being presented to the user; presenting the auditory stimulation to the user at the scheduled timing; and from the electroencephalogram signal, acquiring an event-related potential in a first time range as reckoned from a point in time at which the auditory stimulation is presented. The scheduling step schedules the timing of presenting the auditory stimulation so that, when an amount of luminance change in the output video exceeds a predetermined threshold value, the auditory stimulation is not presented during a second time range as reckoned from a point in time at which the predetermined threshold value is exceeded.

An auditory event-related potential measurement system as another implementation of the present disclosure includes: an auditory stimulation scheduling section configured to schedule a timing of presenting an auditory stimulation so that the auditory stimulation is presented during a period in which a video is being presented to the user from a video output section; an auditory stimulation output section configured to present the auditory stimulation to the user at the scheduled timing; and an electroencephalogram processing section configured to acquire, from an electroencephalogram signal of the user measured by a biological signal measurement section, an event-related potential in a first time range as reckoned from a point in time at which the auditory stimulation is presented. The auditory stimulation scheduling section schedules the timing of presenting the auditory stimulation so that, when an amount of luminance change in the output video exceeds a predetermined threshold value, the auditory stimulation is not presented during a second time range as reckoned from a point in time at which the predetermined threshold value is exceeded.

With an auditory event-related potential measurement apparatus/system according to the present disclosure, during an auditory event-related potential measurement, a video having a size which is considered appropriate is presented as other stimulations in addition to auditory stimulations, thus reducing fluctuations in the auditory event-related potential due to changes in the arousal level of the user, and realizing a highly accurate auditory event-related potential measurement. In particular, it is effective for the measurement of auditory event-related potential in response to auditory stimulations at sound pressures lower than a sound pressure which is generally evaluated to be the UCL. As a result, the accuracy of user hearing evaluation is improved, thus realizing a hearing aid adjustment which does not leave much to be desired by the user, for example.

Hereinafter, the background and findings which led to the present disclosure will be described. Thereafter, the auditory event-related potential measurement system will be described as embodiments, and the construction and operation of the auditory event-related potential measurement apparatus will be described in detail.

Background of the Present Disclosure

As mentioned earlier, in any auditory event-related potential measurement where monotonous auditory stimulations are repeated, the user may not be able to maintain his or her arousal level. This causes changes in the auditory event-related potential waveform that are associated with arousal level fluctuations.

In order to suppress arousal level fluctuations of the user, the inventors have paid attention to a method of presenting visual stimulations (video) during an auditory event-related potential measurement; visual stimulations are of a different modality from that of auditory stimulations. Specifically, the inventors have given thought to a method which, while simultaneously presenting auditory stimulations and visual stimulations (video), measures auditory event-related potentials that are evoked by the auditory stimulations. Examples of videos which can suppress arousal level fluctuations include movies, TV programs such as dramas or sport broadcasting, and so on. However, when any such video is presented, an electroencephalogram that is induced by the video will be mixed as noise, thus making it necessary to somehow reduce this influence. The inventors have decided to present auditory stimulations so as to avoid the timing of any substantial luminance change, e.g., switching of scenes within the video. In this manner, influences of noise components associated with the video are reduced, thus, realizing an auditory event-related potential measurement with a higher accuracy, which is free from the influences of noises due to luminance changes. Although there may be some video-induced electroencephalogram that is caused by higher-order encephalic activities associated with cognition of the content of the video, such will be disregarded in the present disclosure because it permits large individual differences, thus making it impossible to anticipate any component that is induced by the presented video.

FIG. 1A shows an experimental paradigm of a conventional auditory event-related potential measurement. The horizontal axis represents time, against which timings of auditory stimulations are schematically indicated by vertical lines. In order to reduce noises such as the background electroencephalogram through arithmetic mean, auditory stimulations are repetitively presented. For example, assuming that each auditory stimulation has a duration of 100 ms, the stimulation intervals have a mean value of 1 second, and the number of repetitions is 30 times, then, about 30 seconds of time is required for an auditory event-related potential measurement with respect to one frequency, one sound pressure, and one ear.

Figure 1B:
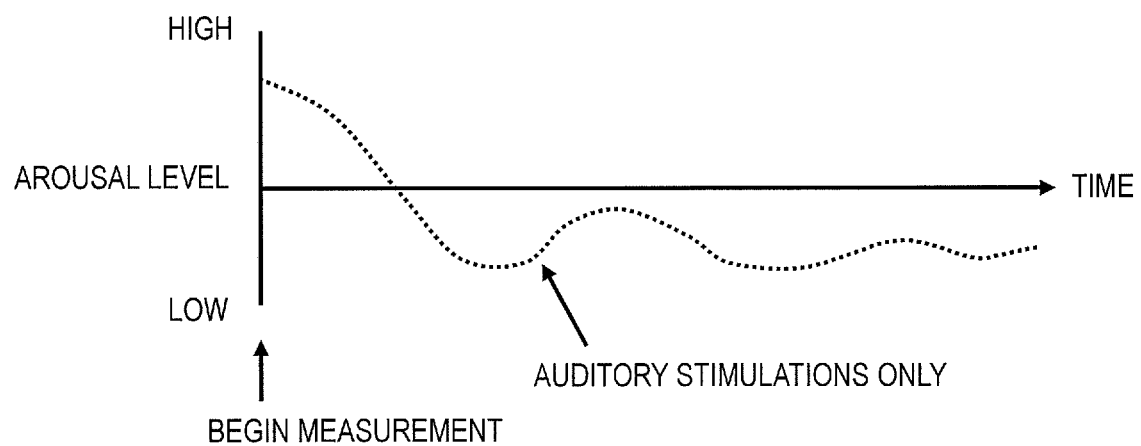

Therefore, in the case of measuring auditory event-related potentials for five frequencies, five sound pressures, and both ears in order to make a hearing evaluation of a user, for example, a simple calculation would indicate that about 25 minutes (30×5×5×2 seconds) is required. Thus, the user needs to keep hearing monotonous auditory stimulations for a total of about 25 minutes, which makes it difficult to maintain his or her arousal level. FIG. 1B shows imaginary arousal level fluctuations of a user during the auditory event-related potential measurement. The horizontal axis represents time, whereas the vertical axis represents the arousal level. FIG. 1B illustrates an imaginary manner in which the arousal level may lower with lapse of time since the beginning of an auditory event-related potential measurement.

Figure 2A:
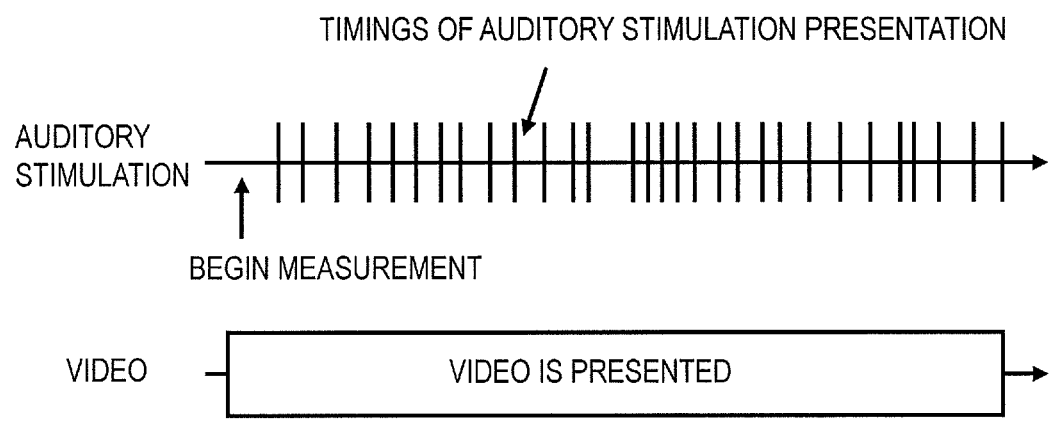
FIGS. 2A and 2B are diagrams showing an auditory event-related potential measurement paradigm where a video is concurrently presented, and imaginary changes in arousal level during an auditory event-related potential measurement.
Figure 2B:
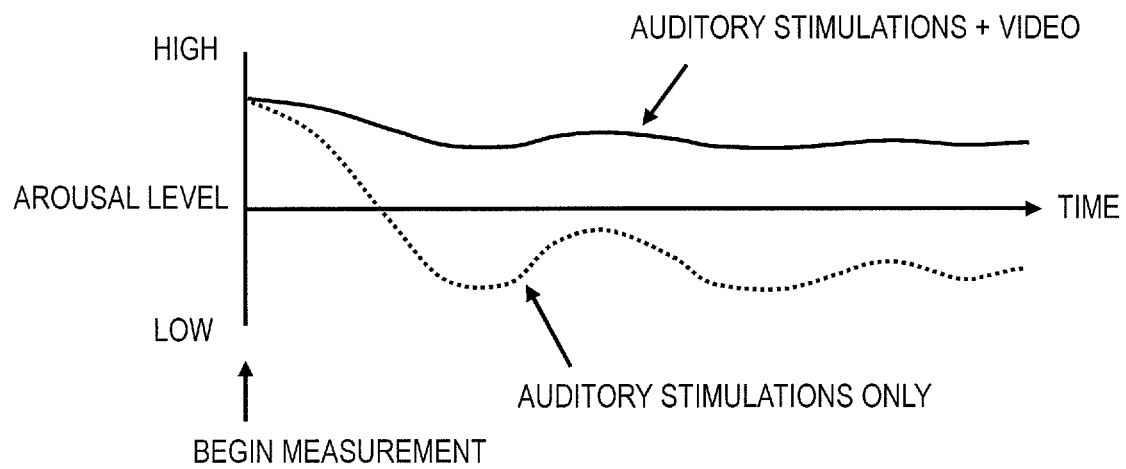

FIG. 2A shows an auditory event-related potential measurement paradigm where a video is concurrently presented. The inventors have paid attention to an method of auditory event-related potential measurement shown in FIG. 2A. In order to suppress a decrease in the arousal level of the user during the auditory event-related potential measurement, auditory stimulations are presented while presenting a video. FIG. 2B shows imaginary arousal level fluctuations of a user during the auditory event-related potential measurement in a similar manner to FIG. 1B. It is considered that, due to the video presentation, decrease in the arousal level of the user is suppressed, so that the arousal level is maintained relatively high.

FIG. 2B only represents an imaginary graph of the arousal level. However, the inventors actually conducted a 10-minute auditory event-related potential measurement with five participants, under conditions with or without video presentation, and a post-measurement questionnaire on the arousal level indicated that all of the participants reported a higher arousal level with the video presentation. This at least implies that a decrease in the arousal level of the user during the auditory event-related potential measurement is reduced by video presentation.

However, in connection with video presentation, a characteristic electroencephalogram will be mixed and become a noise in the auditory event-related potential measurement. Therefore, it is considered difficult to attain a highly accurate auditory event-related potential measurement by merely presenting a video simultaneously with auditory stimulations.

Therefore, the inventors have devised a method of, within an electroencephalogram which is induced by a video, reducing at least the influence of a visual evoked potential (visual evoked potential: VEP) that is induced in response to physical changes in the video. Specifically, the inventors have devised a method which retains timings of luminance change which are acquired in advance by analyzing the video, and controls the timing of presenting auditory stimulations so that no auditory stimulation is presented within a predetermined time range as reckoned from the timing of any luminance change. This makes it possible to measure an auditory event-related potential with reduced influence of the visual evoked potential. Hereinafter, this will be described in detail.

Firstly, a visual evoked potential is a transient electroencephalographic potential that is evoked by flashlight (whose entire luminance changes) or a patterned stimulation (whose luminance distribution changes). Regardless of flashlight or a patterned stimulation, a negative electroencephalogram is evoked at about 70 ms from the stimulation; a positive electroencephalogram at about 100 ms; and a negative electroencephalogram at about 130 ms. Although the latency and amplitude will vary depending on the luminance and intensity of the visual stimulation, there is relatively little influence of individual differences. According to "SHIN SEIRISHIN-RIGAKU" (or "NEW PHYSIOPSYCHOLOGY"), supervised by MIYATA (third edition), vol. 1, p. 115, on the basis of the linked right and left mastoids, a visual evoked potential is predominantly induced from the parietal to the occiput, but is also induced at the central portion, where the auditory event-related potential prevails.

For example, in the video of a movie, or a TV program such as a drama or sport broadcasting, there are timings at which the overall luminance or luminance distribution of the screen undergoes substantial changes, e.g., switching of scenes. Corresponding to the timing of such a luminance change, a visual evoked potential is induced, which will become a noise in the auditory event-related potential measurement.

Figure 3:
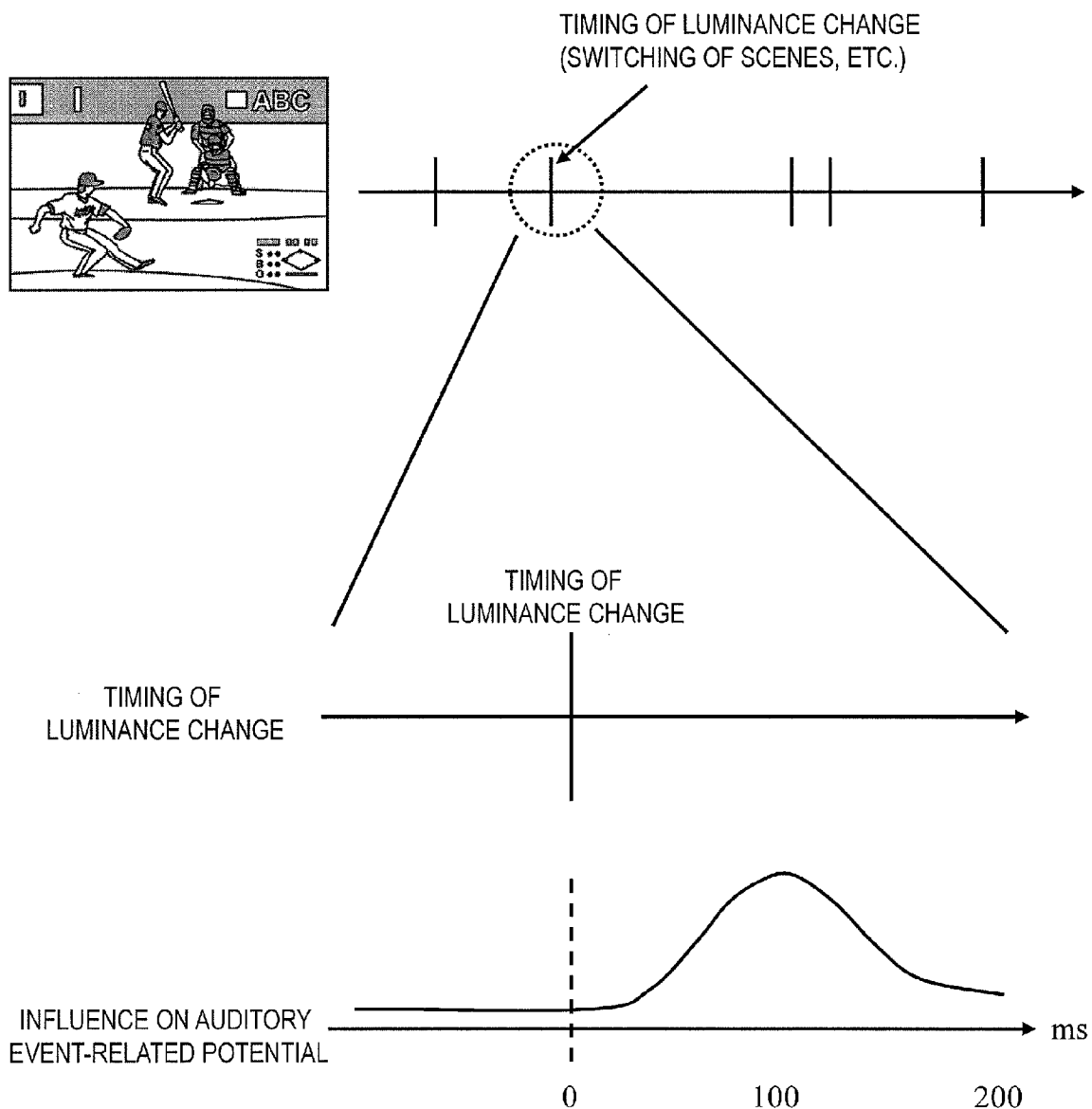
FIG. 3 is a conceptual diagram showing timings of luminance change and the influence, on the auditory event-related potential, of a visual evoked potential in response to a luminance change.

FIG. 3 schematically shows timings of luminance change in a video and the influence, on the auditory evoked potential measurement, of a visual evoked potential that is induced by a particular luminance change. A video sequence likely includes several timings at which a luminance change exceeding a predetermined threshold value occurs. Based on such a timing of luminance change as a starting point, a visual evoked potential is induced. This becomes mixed as a noise, with a peak at about 100 ms based on the luminance change as a starting point. The influence of the visual evoked potential lasts about 200 ms after the timing of luminance change. It is therefore considered that, in order to measure an auditory event-related potential, auditory stimulations may be presented when the influence of such a visual evoked potential is sufficiently low.

A "luminance change" as used in the present specification may include either or both of: a change in the overall luminance of a video; and a change in luminance distribution (which encompasses the case where no change in the average luminance occurs). On this basis, the timing at which a luminance change occurs is referred to as a "timing of luminance change".

As mentioned above, the inventors have devised a method which retains timings of luminance change which are acquired in advance by analyzing the video, and controls the timing of presenting auditory stimulations so that no auditory stimulation is presented within a predetermined time range as reckoned from the timing of any luminance change. The "predetermined time range" may be a range from 100 ms before a timing of luminance change to 200 ms after the timing of luminance change, for example. As a result, the influence of visual evoked potential can be reduced.

Controlling the timing of presenting auditory stimulations might allow the stimulation interval of auditory stimulations to be about several seconds apart, depending on how often luminance changes occur in the video. Taking note of such stimulation intervals, the inventors have furthered their study to find that an auditory event-related potential measurement can be realized which is more accurate than merely controlling the timing of presenting auditory stimulations in accordance with the timings of luminance change in a video. Specifically, the inventors have decided that, when a stimulation interval from an auditory stimulation has lasted a predetermined length or longer, the auditory stimulation that is the first to be presented after the interval of the predetermined length or longer is excluded from an arithmetic mean that is taken for auditory event-related potential calculation.

The reason is that, as is described in a previous document (Naatanen, R, "Attention and brain function", p. 126, 1992), if there has been a stimulation interval of several seconds or more, presumably a large-amplitude component which is irrespective of any sensory stimulation is induced at about 100 ms after the auditory stimulation presentation, and thus is mixed as a noise into the auditory event-related potential.

Conventionally, in trials of event-related potential measurement, any event-related potential that contains noise is excluded. Specifically, based on measured potential data, only those event-related potentials which clearly indicate presence of noise are excluded, e.g., when the amplitude maximum value exceeds ±80 μV. In conventional trials, it has not been commonplace to present any information other than what is the target of measurement (e.g., presenting a video as proposed in the present disclosure), and exclude certain event-related potentials based on the content of the presented information which is not the target of measurement. Note that, since an auditory event-related potential and a visual evoked potential are close in frequency, it is currently difficult to reduce the influence of a visual evoked potential through frequency filtering.

Hereinafter, the auditory event-related potential measurement system will be described in terms of illustrative embodiments according to the present disclosure.

(Embodiment 1)

<Outline of the Auditory Event-related Potential Measurement System>

The auditory event-related potential measurement system according to the present embodiment presents a video during an auditory event-related potential measurement, and in accordance with previously-retained timings of luminance change in the video, controls the timing of presenting an auditory stimulation so that no auditory stimulation is presented within a predetermined time range as reckoned from the timing of any luminance change. As a result, a highly accurate auditory event-related potential measurement is realized, with little fluctuation in the arousal level of the user and the influence of a visual evoked potential evoked by the video being minimized. Moreover, when a stimulation interval from an auditory stimulation has lasted a predetermined length or longer, the auditory stimulation that is the first to be presented after the interval of the predetermined length or longer is excluded from an arithmetic mean that is taken for auditory event-related potential calculation. As a result, the influence of a noise component that is mixed in an electroencephalogram that is evoked by the auditory stimulation that is the first to be presented after the interval can be reduced, whereby a more accurate auditory event-related potential measurement is realized.

In the present embodiment, by providing a probe electrode at the central portion (Cz) and a reference electrode at the right mastoid, an electroencephalogram is measured as a potential difference between the probe electrode and the reference electrode. Note that the level and polarity of a characteristic component of the event-related potential may possibly vary depending on the sites at which electrodes for electroencephalogram measurement are worn, and on the positions at which the reference electrode and the probe electrode are set. However, based on the following description, those skilled in the art should be able to extract a characteristic feature of the event-related potential and perform an auditory event-related potential measurement by making appropriate modifications in accordance with the particular reference electrode and probe electrode used. Such variants are encompassed within the present disclosure.

<Environment of Use>

Figure 4:
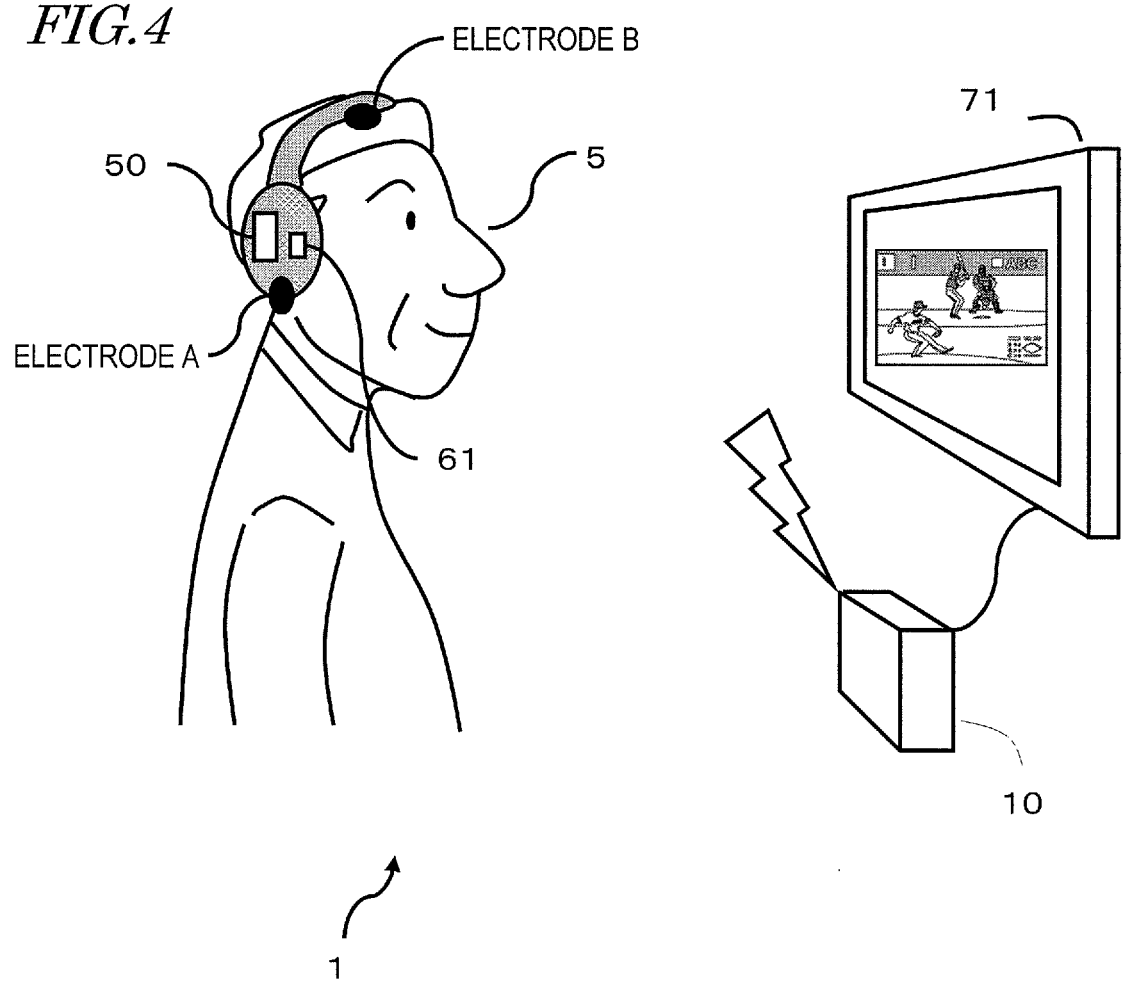
FIG. 4 is a diagram showing a construction and an environment of use for an auditory event-related potential measurement system 1 according to Embodiment 1.

FIG. 4 shows a construction and an environment of use for an auditory event-related potential measurement system 1. The auditory event-related potential measurement system 1 (hereinafter referred to as the "measurement system 1") is illustrated as an example corresponding to the system construction (FIG. 6) of Embodiment 1 described later.

The measurement system 1 is a system for measuring an auditory event-related potential of a user 5 with a high accuracy. An electroencephalogram signal of the user 5 is acquired by a biological signal measurement section 50 which is worn on the head of the user, and is sent in a wired or wireless manner to an auditory event-related potential measurement apparatus 10 (hereinafter referred to as the "measurement apparatus 10").

In a wired or wireless manner, an auditory stimulation output section 61 and a video output section 71 receive auditory stimulation information and video information, respectively, from the measurement apparatus 10, and present an auditory stimulation and a video, respectively, to the user 5. The measurement system 1 shown in FIG. 4 includes the biological signal measurement section 50 and the auditory stimulation output section 61 within the same housing; however, this is only an example. The biological signal measurement section 50 and the auditory stimulation output section 61 may be provided in separate housings.

The biological signal measurement section 50 is a measuring instrument which measures a biological signal of the user. In the present disclosure, one example of the biological signal measurement section 50 may be an electroencephalograph. The biological signal measurement section 50 is connected to at least two electrodes A and B. For example, electrode A is attached to a mastoid of the user 5, whereas electrode B is attached to a central portion (so-called Cz) on the scalp of the user 5. The biological signal measurement section 50 measures an electroencephalogram of the user 5 that corresponds to a potential difference between electrode A and electrode B, and outputs an electroencephalogram signal.

The auditory stimulation output section 61 is headphones or loudspeakers for outputting an auditory stimulation to the user 5, for example.

The video output section 71 is a monitor for presenting a video to the user 5, for example.

While presenting the video of a movie or a TV program to the user 5, the measurement apparatus 10 presents auditory stimulations, and measures an auditory event-related potential. Specifically, in accordance with previously-retained timings of luminance change in the video, the measurement apparatus 10 controls the timing of presenting an auditory stimulation so that no auditory stimulation is presented within a predetermined time range as reckoned from the timing of any luminance change. Moreover, when a stimulation interval from an auditory stimulation has lasted a predetermined length or longer, the auditory stimulation that is the first to be presented after the interval of the predetermined length or longer is excluded from an arithmetic mean that is taken for auditory event-related potential calculation.

<Hardware Construction>

Figure 5:
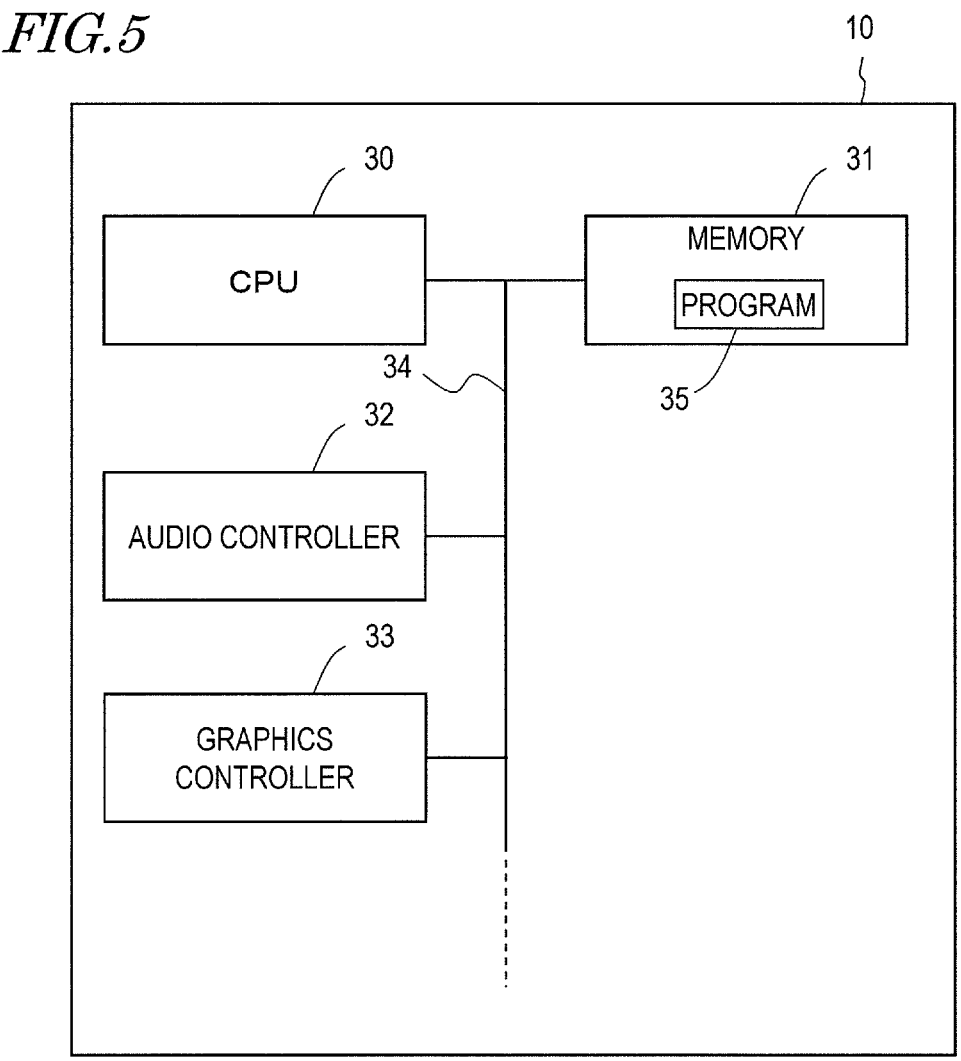
FIG. 5 is a diagram showing the hardware construction of an auditory event-related potential measurement apparatus 10 according to Embodiment 1.

FIG. 5 shows the hardware construction of the measurement apparatus 10 of the present embodiment. The measurement apparatus 10 includes a CPU 30, a memory 31, an audio controller 32, and a graphics controller 33. The CPU 30, the memory 31, the audio controller 32, and the graphics controller 33 are connected to one another via a bus 34, so that data exchange among them is possible.

The CPU 30 executes a computer program 35 which is stored in the memory 31. A processing procedure which is illustrated by a subsequently-described flowchart is described in the computer program 35. In accordance with the computer program 35, the measurement apparatus 10 performs a process of controlling the entire measurement system 1, e.g., auditory stimulation generation, video reproduction, detection of luminance changes in video, controlling the timings of presenting auditory stimulations, and determination of ignorable trials. This process will be described in detail later.

In accordance with an instruction from the CPU 30, the audio controller 32 outputs via the auditory stimulation output section 61 auditory stimulations to be presented, each at a designated timing and with a designated sound pressure and duration.

In accordance with an instruction from the CPU 30, the graphics controller 33 outputs a video via the video output section 71.

Note that the measurement apparatus 10 may be implemented as a piece of hardware (e.g., a DSP) consisting of a semiconductor circuit having a computer program therein. Such a DSP can realize all functions of the aforementioned CPU 30, memory 31, audio controller 32, and graphics controller 33 on a single integrated circuit.

The aforementioned computer program 35 may be distributed on the market in the form of a product recorded on a storage medium such as a CD-ROM, or transmitted through telecommunication lines such as the Internet. Upon reading the computer program 35, a device having the hardware shown in FIG. 5 (e.g., a PC) is able to function as the measurement apparatus 10 of the present embodiment.

<Construction of the Measurement System 1>

Figure 6:
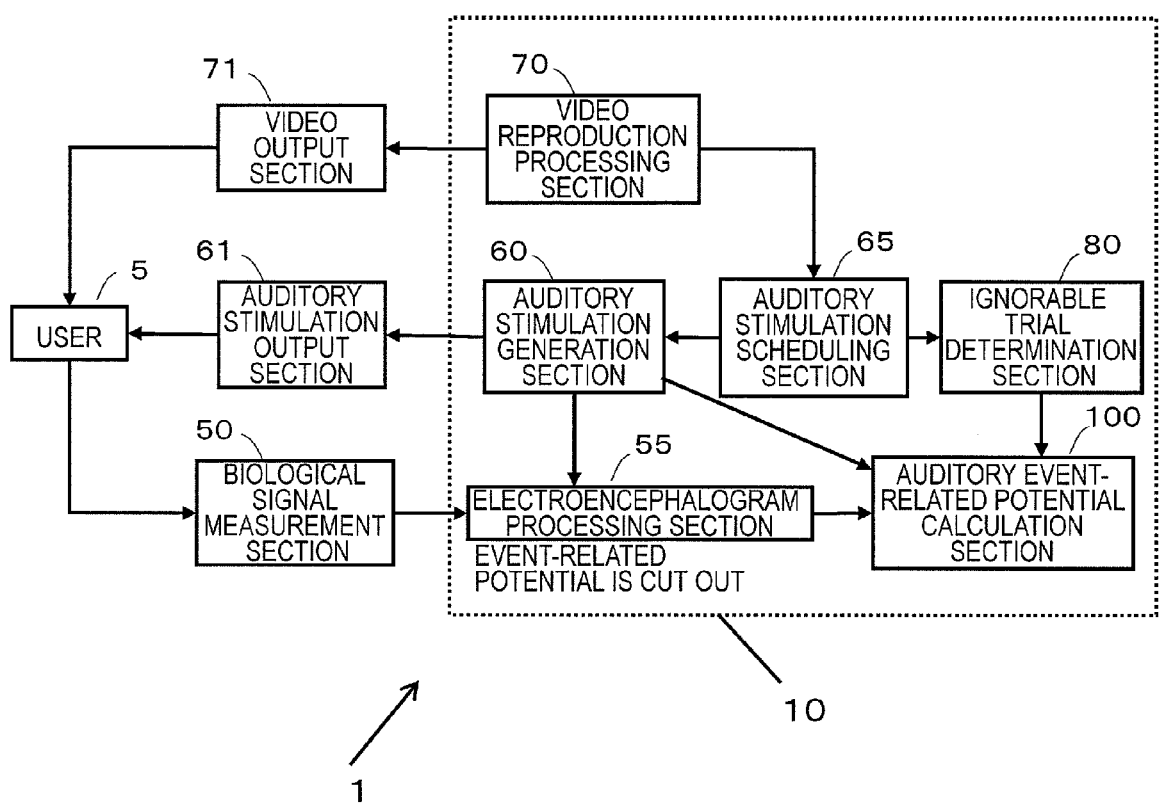
FIG. 6 is a diagram showing the functional block construction of an auditory event-related potential measurement system 1 according to Embodiment 1.

FIG. 6 shows the functional block construction of the measurement system 1 of the present embodiment. The measurement system 1 includes the biological signal measurement section 50, the auditory stimulation output section 61, the video output section 71, and the measurement apparatus 10. The component elements of the measurement system 1 are interconnected in a wired or wireless manner. The user 5 block is illustrated for ease of description.

The measurement apparatus 10 includes an electroencephalogram processing section 55, an auditory stimulation generation section 60, an auditory stimulation, scheduling section 65, a video reproduction processing section 70, an ignorable trial determination section 80, and an auditory event-related potential calculation section 100.

Note that it suffices if the measurement system 1 at least includes the auditory stimulation generation section 60, the electroencephalogram processing section 55, and the auditory stimulation scheduling section 65. For example, those component elements which are present in the measurement system 1 shown in FIG. 6 but are missing from a measurement system that only includes the auditory stimulation generation section 60, the electroencephalogram processing section 55, and the auditory stimulation scheduling section 65 may exist as external component elements to the measurement system. Each of the auditory stimulation generation section 60, the electroencephalogram processing section 55, and the auditory stimulation scheduling section 65 can exchange information with other component elements based on interconnection as shown in FIG. 6. As a result, the operation of the present embodiment can be realized.

The auditory stimulation generation function of the auditory stimulation generation section 60 and the video reproduction function of the video reproduction processing section 70 may be realized by other devices. The ignorable trial determination section 80 may be provided for a more accurate auditory event-related potential measurement, but is not essential. In the case where the ignorable trial determination section 80 is omitted and where there is no need to take an arithmetic mean of event-related potentials, the auditory event-related potential calculation section 100 is not essential.

The respective functional blocks of measurement apparatus 10 correspond to functions which are occasionally realized by the CPU 30, the memory 31, the audio controller 32, and the graphics controller 33 as a whole when the program described in connection with FIG. 5 is executed.

Hereinafter, the component elements of the measurement system 1 will be described.

<Video Reproduction Processing Section 70>

In a hard disk drive not shown, for example, the video reproduction processing section 70 previously retains data of a video (content) to be presented to the user. The video reproduction processing section 70 reproduces that video content. A video content is information containing a chronological sequence of a plurality of at least partially differing images: for example, a movie, or a TV program such as a drama or sport broadcasting. For the purpose of suppressing fluctuations in the arousal level of the user 5, the user 5 may be allowed to select a content according to the level of interest of the user 5.

The present embodiment assumes that the video content does not contain any audio information. However, the video content may contain some audio information, in which case the audio information contained in the video content may be prohibited from being output by, for example, the video reproduction processing section 70 exerting control for not allowing the audio to be output through the loudspeakers.

Furthermore, the video reproduction processing section 70 sends previously-retained timings of luminance change in the video to the auditory stimulation scheduling section 65. Note that the auditory stimulation scheduling section may also be referred to as the "auditory stimulation timing determination section".

FIGS. 7A and 78 show examples of timings of luminance change. As shown in FIG. 7A, a list of timings of luminance change that is described in units of milliseconds may be employed, with the beginning of video reproduction being 0 ms.

Note that a timing of luminance change may be detected by analyzing the video at the video reproduction processing section 70. In that case, it will be necessary to analyze the video at least 200 ms before presenting the video to the user 5 via the video output section 71, and detect timings of luminance change.

As a method of detecting timings of luminance change, for example, a frame-to-frame luminance difference may be calculated for each pixel, and an integral of such differences may be compared against a previously-set predetermined threshold value; when the integral becomes greater than the threshold value, that timing may be recorded. In other words, given a plurality of images composing a video content, a comparison is made for each of the pixels contained in a plurality of successive images, and if there is a predetermined luminance change or more, it may be determined that a luminance change has occurred. The luminance change comparison may be made with respect to each single pixel, or with respect to each group of pixels. As a result, the video reproduction processing section 70 is able to generate data which defines associations between the video and timings of luminance change.

<Video Output Section 71>

The video output section 71 is connected to the video reproduction processing section 70 in a wired or wireless manner, and outputs a video which has been subjected to a reproduction process by the video reproduction processing section 70. During a period of measuring an auditory event-related potential, the video output section 71 outputs a video for as long a time as possible. This enables the user 5 to maintain his or her arousal level.

<Auditory Stimulation Scheduling Section 65>

Referring to the timings of luminance change received from the video reproduction processing section 70, the auditory stimulation scheduling section 65 determines points in time to output auditory stimulations. The points in time to output auditory stimulations will also be referred to as a "schedule".

The auditory stimulation scheduling section 65 sends the schedule of auditory stimulations to the auditory stimulation generation section 60 and the ignorable trial determination section 80. The schedule of auditory stimulations is based on the premise that the point in time at which the video reproduction processing section 70 begins to reproduce the video is 0 ms.

First, the auditory stimulation scheduling section determines an initial schedule based on an auditory stimulation interval which is arbitrarily set. An initial schedule sequence shown in FIG. 7B indicates schedule values in the case where the stimulation interval is 300±50 ms, for example. Then, timings of luminance change as shown in FIG. 7A may be received from the video reproduction processing section 70. In this case, the auditory stimulation scheduling section 65 changes the schedule of auditory stimulations so that no auditory stimulation is presented within a predetermined time range as reckoned from the timing of any luminance change, for example. It is possible to change the interval between auditory stimulations depending on the event-related potential acquired. Without ensuring that an auditory stimulation be presented after a predetermined interval or more has elapsed from the timing of luminance change, it might be impossible to determine the acquired event-related potential to be a signal that has occurred in response to the luminance change or a signal that has occurred in response to the auditory stimulation.

The predetermined time range may be a zone from 100 ms before a luminance change to 200 ms after a luminance change, for example. The reason for the inclusion of 100 ms before a luminance change to 0 ms is as follows. Suppose that an auditory stimulation was presented 100 ms before a luminance change. In response to this auditory stimulation, an auditory event-related potential will be evoked in about 200 ms, i.e., 100 ms after the luminance change. On the other hand, in response to a visual stimulation at the time of luminance change (0 ms), a visual event-related potential will be evoked in about 100 ms. In other words, 100 ms after the luminance change, the auditory event-related potential will collide with the visual event-related potential. This is the reason why it is ensured that no auditory stimulation is presented at a point 100 ms before a luminance change or later.

The schedule of auditory stimulations may be changed as follows. For example, as in Case 1 of FIG. 7B, if an initial schedule value of an auditory stimulation happens to be within a predetermined time range as reckoned from a timing of luminance change, that auditory stimulation may be skipped. Or, as in Case 2 of FIG. 78, if an initial schedule value of an auditory stimulation happens to be within a predetermined time range as reckoned from a timing of luminance change, presentation of that auditory stimulation may be suspended until the predetermined time range elapses, with all subsequent stimulations being delayed from the initial schedule by that same waiting time.

In Case 1, the interval from a timing of luminance change to a next auditory stimulation that is presented is random; therefore, Case 1 is less susceptible to the influence of any component that is specific to a luminance change. In Case 2, the next auditory stimulation is presented as soon as the predetermined time range elapses from a timing of luminance change, and thus Case 2 requires a shorter evaluation time than does Case 1.

FIG. 8 is a schematic diagram of the above two schedule changing methods. According to the schedule changing method of Case 1, any auditory stimulation whose initial schedule value falls within a predetermined time range as reckoned from a timing of luminance change is skipped. According to the schedule changing method of Case 2, the schedule is prolonged until the lapse of the predetermined time range, and the subsequent auditory stimulations are also delayed by that prolonged time.

<Auditory Stimulation Generation Section 60>

From the auditory stimulation scheduling section 65, the auditory stimulation generation section 60 acquires schedule information concerning the timing of presenting an auditory stimulation, and determines information of an auditory stimulation to be presented to the user at that timing. The auditory stimulation information includes which of the right or left ear of the user 5 the auditory stimulation is to be presented to, and the frequency and sound pressure of the auditory stimulation to be presented. The right or left ear, the frequency, and the sound pressure of the auditory stimulation to be presented are determined.

For example, a random determination may be made under the following constraints.

No auditory stimulation of the same frequency and the same sound pressure as an immediately previous auditory stimulation is selected.

The right or left ear is preferably selected in a random order. However, it is preferable that not more than four auditory stimulations are presented successively to either the right or left ear.

By doing so, the influence of taming (habituation) of the electroencephalogram due to successive presentation of auditory stimulations to the same ear and at the same frequency is reduced, whereby a highly accurate auditory event-related potential measurement is realized.

Then, the auditory stimulation generation section 60 generates an audio signal of the determined auditory stimulation, and sends it to the auditory stimulation output section 61 according to the timing of auditory stimulation presentation received from the auditory stimulation scheduling section 65. The auditory stimulation may be a toneburst sound having a rise and fall of 3 ms, for example. The duration of an auditory stimulation is set to be e.g. 25 ms or more, so that an auditory event-related potential will be stably induced. Moreover, at the timing of sending auditory stimulation information to the auditory stimulation output section 61, the auditory stimulation generation section 60 outputs a trigger to the electroencephalogram processing section 55. This trigger is used when cutting out an event-related potential in response to an auditory stimulation at the electroencephalogram processing section 55. The auditory stimulation generation section 60 also sends the auditory stimulation information to the auditory event-related potential calculation section 100.

<Auditory Stimulation Output Section 61>

The auditory stimulation output section 61 is connected to the auditory stimulation generation section 60 in a wired or wireless manner. The auditory stimulation output section 61 reproduces auditory stimulation data which is generated by the auditory stimulation generation section 60, and presents it to the user 5.

<Biological Signal Measurement Section 50>

The biological signal measurement section 50 measures a biological signal of the user 5. The biological signal measurement section 50 measures a biological signal of the user 5, which corresponds to a potential difference between the reference electrode and the probe electrode worn by the user 5. In the present embodiment, the biological signal of the user 5 is an electroencephalogram.

The biological signal measurement section 50 may apply frequency filtering with an appropriate cutoff frequency to the electroencephalogram data. Then, the biological signal measurement section 50 sends that electroencephalogram data to the electroencephalogram processing section 55. In the case where a band-pass filter is used as the frequency filter, the cutoff frequency may be set so as to pass e.g. 5 Hz to 15 Hz. It is assumed that the user 5 has worn the electroencephalograph in advance. The probe electrode for electroencephalogram measurement is attached at the central portion Cz, for example.

<Electroencephalogram Processing Section 55>

From the electroencephalogram data received from the biological signal measurement section 50, the electroencephalogram processing section 55 cuts out an event-related potential in a predetermined zone (e.g., a zone from 100 ms before the auditory stimulation presentation to 400 ms after the auditory stimulation presentation), based on the trigger received from the auditory stimulation generation section 60 as a starting point.

The zone to cut out may be any zone that contains a targeted component of the auditory event-related potential. For instance, a negative component (N1 component) appearing in a zone from 50 ms to 150 ms based on a point of auditory stimulation will be taken as an example. The zone to cut out may be a zone from 100 ms before the auditory stimulation presentation to 400 ms after the auditory stimulation presentation as mentioned above, or may be a zone from 50 ms to 150 ms based on the point of auditory stimulation. The electroencephalogram processing section 55 sends the cutout event-related potential to the auditory event-related potential calculation section 100.

Note that a "cutout event-related potential" does not only mean a piece of electroencephalogram data which has actually been extracted from a predetermined zone of a measured electroencephalogram signal, but also encompasses a piece of electroencephalogram data containing the necessary potential in an extractable state, which does not need to have actually been extracted. For example, a necessary event-related potential is ready extractable so long as there are the electroencephalogram signal and zone information identifying a predetermined zone within that electroencephalogram signal. It can be said that, by acquiring these, the electroencephalogram processing section 55 is able to obtain a "cutout event-related potential".

The electroencephalogram processing section 55 sends the acquired event-related potential to the auditory event-related potential calculation section 100.

<Ignorable Trial Determination Section 80>

The ignorable trial determination section 80 receives information of the schedule of auditory stimulations from the auditory stimulation scheduling section 65. If the stimulation interval is equal to or greater than a predetermined length, the ignorable trial determination section 80 designates, as an ignorable trial, the auditory stimulation that is the first to be presented thereafter.

The predetermined length may be a fixed value, or determined according to a previously-set stimulation interval for auditory stimulations. In the case where it is a fixed value, as is introduced in a document (Naatanen, "Attention and brain function", p. 126, 1992), it may be set at 2 seconds, at which a noise component that is induced irrespective of the type of sensory input will occur, or it may be set at 6 seconds, at which the noise component will exceed the amplitude of any event-related potential that is related to a sensory stimulation. Alternatively, it may be set to a multiple of the maximum value (i.e., 350 ms in the case where the stimulation interval is 300±50 ms) of the stimulation interval by a constant which is two or more. Then, the ignorable trial determination section 80 sends the information of the ignorable trial to the auditory event-related potential calculation section 100. The ignorable trial information is a piece of information having an ignorable trial flag that identifies the auditory stimulation to be excluded.

<Auditory Event-related Potential Calculation Section 100>

Based on the auditory stimulation information received from the auditory stimulation generation section 60 and the ignorable trial information received from the ignorable trial determination section 80, the auditory event-related potential calculation section 100 takes an arithmetic mean of the event-related potentials of those trials which do not have an ignorable trial flag set thereto, from among the event-related potentials received from the electroencephalogram processing section 55.

In the present specification, it is assumed that an arithmetic mean of event-related potentials in response to a plurality of auditory stimulations sharing the same characteristic feature, e.g., having the same frequency, is to be calculated. Therefore, the arithmetic mean herein permits methods other than taking an arithmetic mean of the event-related potentials in response to all presented auditory stimulations. It is meant that "same frequency" is said of any two auditory stimulations having an equal frequency, or any two auditory stimulations having frequencies with a difference that is not aurally distinguishable to humans, with possible variations of 5 Hz, for example. On the other hand, different frequencies would mean frequencies with a difference that is aurally distinguishable to humans.

FIG. 9 shows examples of information which the auditory event-related potential calculation section 100 receives from the auditory stimulation generation section 60 the ignorable trial determination section 80, and the electroencephalogram processing section 55. For each trial number, an association is defined between the auditory stimulation information, ignorable trial flag, and event-related potential. Then, an arithmetic mean of the event-related potentials of those trials which do not have an ignorable trial flag set thereto is taken, with respect to either the right or left ear, each frequency, and each sound pressure, for example.

In FIG. 9, "trial number" denotes a serial number of each auditory stimulation that has been presented since auditory event-related potential measurement was begun. In the auditory stimulation information, "right or left" indicates a number for identifying the right or left ear to which each auditory stimulation is presented, e.g., 1 for the right ear, and 2 for the left ear; "frequency" indicates the frequency of each auditory stimulation in units of Hz; and "sound pressure" indicates the sound pressure of each auditory stimulation in units of dBHL. The "ignorable trial flag" is a flag for any ignorable trial as determined by the ignorable trial determination section 80, e.g., 1 for any ignorable trial, and 0 for any non-ignorable trial. The "event-related potential" is an event-related potential of the user 5 which is cut out by the electroencephalogram processing section 55. Although FIG. 9 shows schematically waveforms, the event-related potential data is received as an array of number of sampling points×number of measurement channels, for example.

Note that, as described above, the ignorable trial determination section 80 is not essential, but may be omitted. In that case, the auditory event-related potential calculation section 100 acquires each point in time at which an auditory stimulation was output from the auditory stimulation output section 61. Among the event-related potentials in response to the plurality of auditory stimulations acquired by the electroencephalogram processing section 55, an arithmetic mean is taken of the event-related potentials excluding those in response to auditory stimulations whose time interval from an immediately previous auditory stimulation is equal to or greater than a predetermined time.

<Processing Flow of the Measurement System 1>

Figure 10:
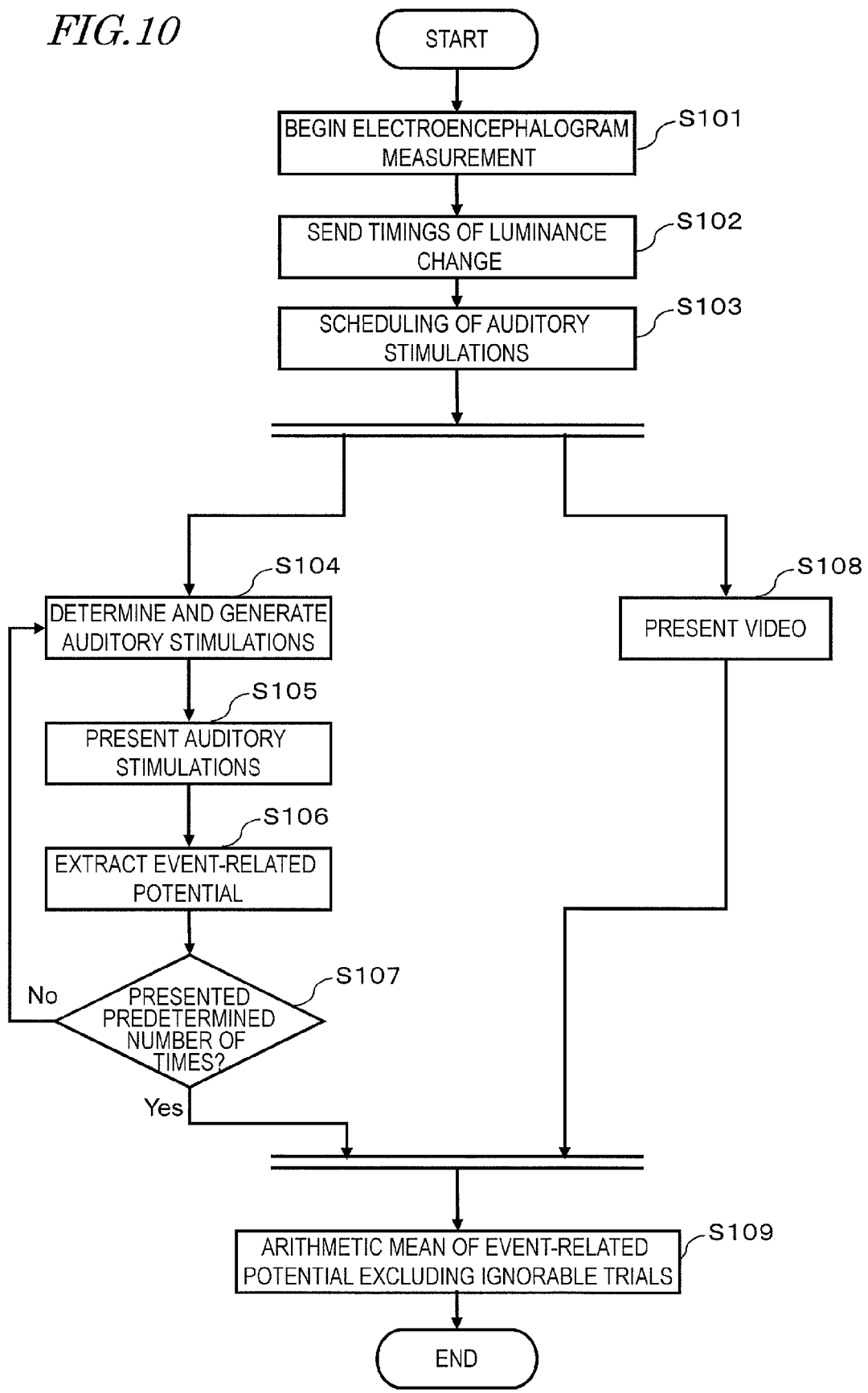
FIG. 10 is a flowchart showing a procedure of processing performed by the auditory event-related potential measurement system 1.

Next, with reference to FIG. 10, a processing procedure which is performed in the measurement system 1 of FIG. 6 will be described. FIG. 10 is a flowchart showing a procedure of processing by the measurement system 1.

At step S101, the biological signal measurement section 50 measures an electroencephalogram of the user 5 as a biological signal. Then, the biological signal measurement section 50 applies frequency filtering with an appropriate cutoff frequency to the electroencephalogram data, and sends continuous electroencephalogram data to the electroencephalogram processing section.

At step S102, the video reproduction processing section 70 sends timings of luminance change in the video content, which are previously-retained in the video reproduction processing section 70, to the auditory stimulation scheduling section 65.

At step S103, the auditory stimulation scheduling section 65 performs scheduling of auditory stimulations, based on the timing of luminance change received from the video reproduction processing section 70 and a previously-set auditory stimulation interval. Then, the auditory stimulation scheduling section 65 sends the schedule of auditory stimulations to the auditory stimulation generation section 60 and the ignorable trial determination section 80.

Scheduling of auditory stimulations is performed in the following procedure. First, based on a previously-set auditory stimulation interval, an initial schedule is determined. Next, the schedule of auditory stimulations is changed so that no auditory stimulation is presented within a predetermined time range as reckoned from the timing of any luminance change, which is received from the video reproduction processing section 70. As for the method of changing the schedule, for example, if an initial schedule value of an auditory stimulation happens to be within a predetermined time range as reckoned from a timing of luminance change, that auditory stimulation may be skipped (Case 1 in FIG. 7B). Alternatively, for example, if an initial schedule value of an auditory stimulation happens to be within a predetermined time range as reckoned from a timing of luminance change, presentation of that auditory stimulation may be suspended until the predetermined time range elapses, with all subsequent stimulations being delayed from the initial schedule by that same waiting time (Case 2 in FIG. 7B).

At step S104, the auditory stimulation generation section 60 determines information of an auditory stimulation to be output at a timing for stimulation presentation which is received from the auditory stimulation scheduling section 65. The auditory stimulation information includes which of the right or left ear of the user 5 the presentation is to be made, as well as the frequency and sound pressure of the auditory stimulation to be presented. That is, the right or left ear, frequency, and sound pressure for the auditory stimulation to be presented are determined. Then, the auditory stimulation generation section 60 generates an auditory stimulation as determined, and sends it to the auditory stimulation output section 61 according to the schedule of auditory stimulations. Moreover, at the timing of sending auditory stimulation information to the auditory stimulation output section 61, the auditory stimulation generation section 60 outputs a trigger to the electroencephalogram processing section 55. The auditory stimulation generation section 60 also sends the auditory stimulation information to the auditory event-related potential calculation section 100.

At step S105, the auditory stimulation output section 61 reproduces the auditory stimulation data which is generated by the auditory stimulation generation section 60, and presents it to the user 5.

At step S106, from the electroencephalogram data received from the biological signal measurement section 50, the electroencephalogram processing section 55 cuts out an event-related potential in a predetermined zone (e.g., a zone from 100 ms before the auditory stimulation presentation to 400 ms after the auditory stimulation presentation), based on the trigger received from the auditory stimulation generation section 60 as a starting point. Then, the electroencephalogram processing section 55 sends the event-related potential to the auditory event-related potential calculation section 100.

Step S107 is a branching based on whether the auditory stimulation presentation and event-related potential extraction at steps S104 to S106 has been performed a predetermined number of times, which is previously set. For example, assuming that 30 times of repetition are made at three sound pressures for each of five frequencies with respect to each of the right and left ears, the predetermined number of times is 900 times (2×5×3×30). If Yes at step S108, control proceeds to step S110; if No, control returns to step S105 to repeat the auditory stimulation presentation and event-related potential extraction.

At step S108, the video reproduction processing section 70 reproduces a video content which is previously-retained in the video reproduction processing section 70, and presents it to the user 5 via the video output section 71. The video content may be a movie, or a TV program such as a drama or sport broadcasting, for example. In order to suppress fluctuations in the arousal level of the user 5, the user 5 may be allowed to select a content according to the level of interest of the user 5. The present embodiment assumes that the video content is presented with no sounds.

At step S109, based on the auditory stimulation information received from the auditory stimulation generation section 60, the schedule information of auditory stimulation presentation received from the auditory stimulation scheduling section 65, and the ignorable trial information received from the ignorable trial determination section 80, the auditory event-related potential calculation section 100 takes an arithmetic mean of the event-related potentials of those trials which do not have an ignorable trial flag set thereto, from among the event-related potentials received from the electroencephalogram processing section 55.

In the present disclosure, step S109 is not essential because, through the processes from steps S101 to S108 including video presentation, the user 5 has received auditory stimulations at a relatively high arousal level, and the auditory event-related potentials evoked by the auditory stimulations have a high accuracy, with reduced influence of visual stimulations. It must be noted that the process of step S109 is introduced for a further enhanced accuracy.

With the measurement system 1 of the present embodiment, a video is presented during an auditory event-related potential measurement, and any auditory stimulation is presented at a timing which does not fall within a predetermined time range as reckoned from a timing of luminance change in the video. Moreover, when a stimulation interval from an auditory stimulation has lasted a predetermined length or longer, the auditory stimulation that is the first to be presented after the interval of the predetermined length or longer is excluded from the arithmetic mean. As a result, a highly accurate auditory event-related potential measurement is realized, with little fluctuation in the arousal level of the user and little influence of a visual evoked potential evoked by the video. As a result, the accuracy of user hearing evaluation is improved, thus realizing a hearing aid adjustment which does not leave much to be desired by the user, for example.

Although the present embodiment does not accumulate results of auditory event-related potential measurement, a database for result accumulation may be additionally provided to accumulate results.

(Embodiment 2)

In the measurement system 1 of Embodiment 1, in accordance with the timings of luminance change in a video which is concurrently presented with auditory stimulations, timings of auditory stimulation presentation are scheduled so that no auditory stimulation is presented within a predetermined time range as reckoned from the timing of any luminance change. Moreover, when a stimulation interval from an auditory stimulation has lasted a predetermined length or longer, the auditory stimulation that is the first to be presented after the interval of the predetermined length or longer is excluded from the arithmetic mean, thereby excluding any noise component that is induced irrespective of the sensory input. Owing to these, a highly accurate auditory event-related potential measurement is realized while reducing a decrease in the arousal level of the user.

In the present embodiment, when the stimulation interval from an auditory stimulation has lasted a predetermined length or longer, an auditory stimulation of a different frequency (referred to as a "dummy auditory stimulation" in the present embodiment) from that of the target of auditory event-related potential measurement is presented. Presenting a dummy auditory stimulation ensures that a noise component that is induced irrespective of the sensory input when the Stimulation interval from an auditory stimulation has lasted a predetermined length or longer is not mixed in the auditory event-related potential for measurement.

Figure 11:
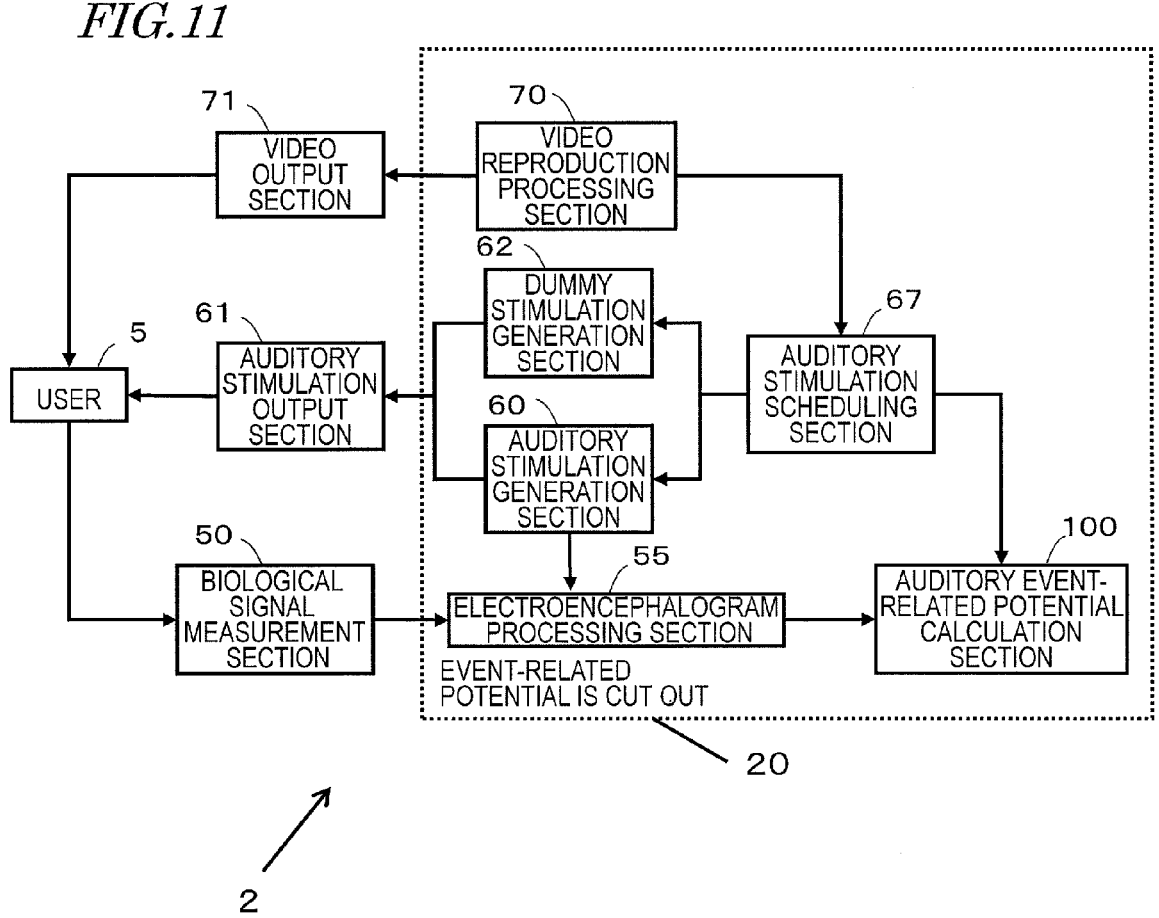
FIG. 11 is a diagram showing the functional block construction of an auditory event-related potential measurement system 2 according to Embodiment 2.

FIG. 11 shows the functional block construction of an auditory event-related potential measurement system 2 of the present embodiment (hereinafter referred to as the "measurement system 2"). The measurement system 2 includes a biological signal measurement section 50, an auditory stimulation output section 61, a video output section 71, and an auditory event-related potential measurement apparatus 20. Any block that has an identical counterpart in FIG. 6 will be denoted by a like reference numeral, with its description omitted. Note that the hardware construction of the auditory event-related potential measurement apparatus 20 is as shown in FIG. 5. By executing a program defining processes that are different from those of the program 35 described in Embodiment 1, the auditory event-related potential measurement apparatus 20 of the present embodiment as shown in FIG. 11 is realized.

Differences of the auditory event-related potential measurement apparatus 20 of the present embodiment from the measurement apparatus 10 of Embodiment 1 are that a dummy stimulation generation section 62 is additionally provided; the ignorable trial determination section 80 is omitted; and an auditory stimulation scheduling section 67 having a different function from that of the auditory stimulation scheduling section 65 according to Embodiment 1 is provided. The auditory stimulation scheduling section 67 switches its process so that, when the stimulation interval from an auditory stimulation has lasted a predetermined length or longer, a dummy auditory stimulation is presented from the dummy stimulation generation section 62.

Hereinafter, the dummy stimulation generation section 62 and the auditory stimulation scheduling section 67 will be described.

The dummy stimulation generation section 62 generates an auditory stimulation of a different frequency from that of the target of auditory event-related potential measurement, and presents the generated auditory stimulation as a "dummy stimulation" to the user 5, via the auditory stimulation output section 61. For example, if 500 Hz, 1000 Hz, 2000 Hz, and 4000 Hz are the frequencies which are the target of auditory event-related potential measurement, an auditory stimulation of a frequency that is outside this frequency range for measurement is generated, e.g., 250 Hz or 8000 Hz. The sound pressure of this auditory stimulation may be set within a range of sound pressure that is the target of auditory event-related potential measurement. By using an auditory stimulation of a frequency outside the frequency range for measurement as a dummy stimulation, the influence of taming on the response to auditory stimulations that are the target of measurement can be eliminated. Since there is no need to measure an event-related potential that is evoked by the dummy stimulation, it is not necessary to output a trigger from the dummy stimulation generation section 62 to the electroencephalogram processing section 55.

Similarly to the auditory stimulation scheduling section 65, the auditory stimulation scheduling section 67 performs scheduling of auditory stimulations by referring to the timings of luminance change which are received from the video reproduction processing section 70. The scheduling of auditory stimulations is done according to Case 2 of FIG. 8. Then, if the stimulation interval from an auditory stimulation is greater than a predetermined length, the schedule of auditory stimulations is sent to the dummy stimulation generation section 62, and if the stimulation interval is equal to or less than the predetermined length, the schedule of auditory stimulations is sent to the auditory stimulation generation section 60. The predetermined length may be a fixed value, or determined according to a previously-set stimulation interval for auditory stimulations. In the case where it is a fixed value, it may be set at 2 seconds, as is stated in a document (Naatanen, R, "Attention and brain function", p. 126, 1992); herein, "2 seconds" represents the number of seconds at which a noise component that is induced irrespective of the type of sensory input will occur. Alternatively, it may be set at 6 seconds, as is stated in the same document; herein, "6 seconds" represents the number of seconds at which the noise component will exceed the amplitude of any event-related potential that is related to a sensory stimulation. Alternatively, it may be set to a multiple of the maximum value (i.e., 350 ms in the case where the stimulation interval is 300±50 ms) of the stimulation interval by a constant which is two or more.

The dummy stimulation and an auditory stimulation to be presented immediately thereafter may be at an interval which is shorter than the aforementioned predetermined length but is longer than an average interval between any two adjacent auditory stimulations in the initial schedule, for example.

Next, with reference to the flowchart of FIG. 12, an overall procedure of processing by the measurement system 2 will be described.

Figure 12:
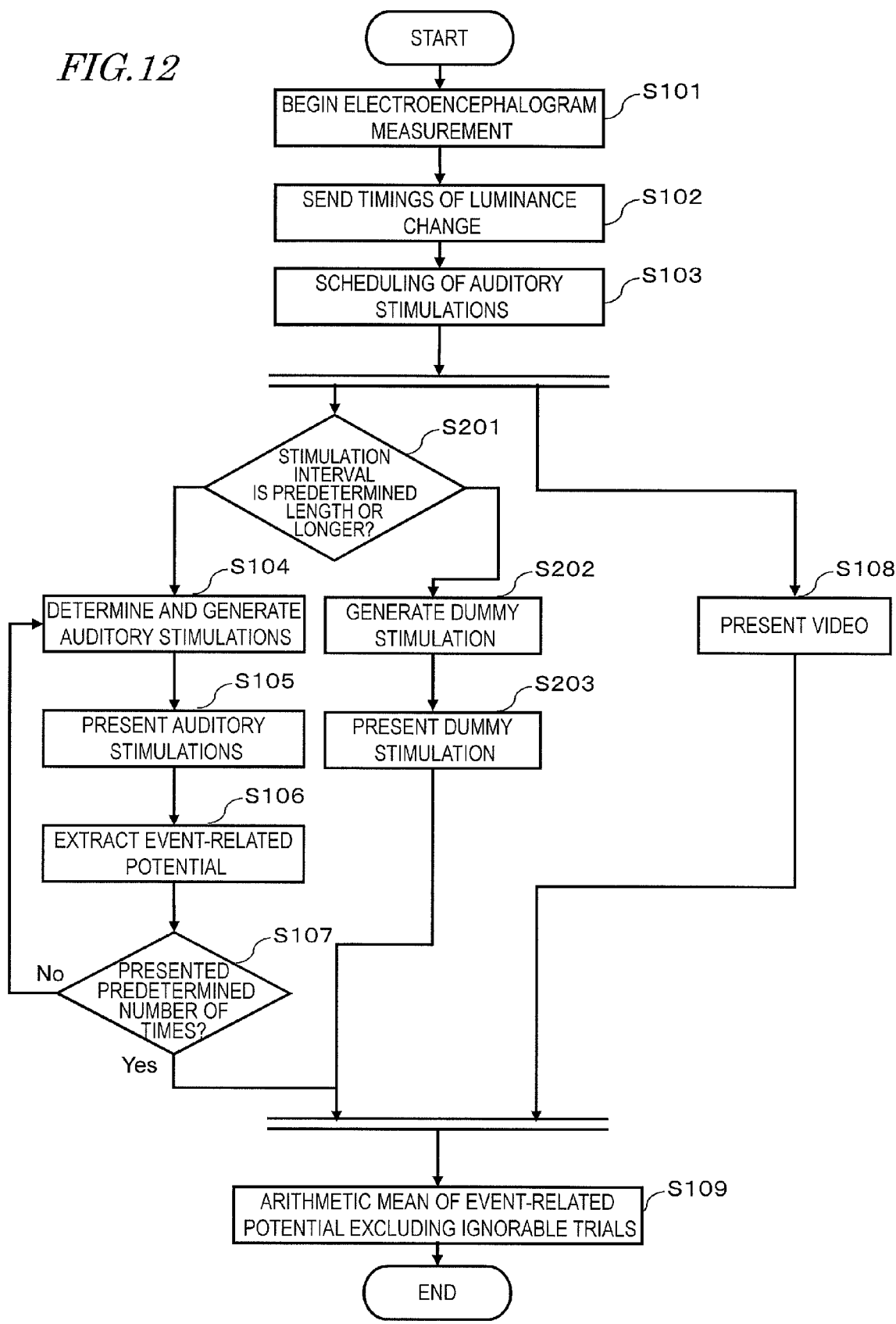
FIG. 12 is a flowchart showing a procedure of processing performed by the auditory event-related potential measurement system 2.

FIG. 12 shows a processing procedure by the measurement system 2 of the present embodiment. In FIG. 12, any step which performs an identical process to that of the measurement system 1 (FIG. 10) will be denoted by a like reference numeral, with its description omitted.

The processes of the measurement system 2 of the present embodiment differ from the processes of the measurement system 1 of Embodiment 1 with respect to steps S201 to S203. The other steps have already been described in connection with FIG. 10, and the description thereof is omitted.

Step S201 is a branching based on whether the stimulation interval from an auditory stimulation as scheduled by the auditory stimulation scheduling section 67 at step S103 is greater than the predetermined length. If it is greater than the predetermined length, control proceeds to step S202; if it is equal to or less than the predetermined length, control proceeds to step S104.

At step S202, the dummy stimulation generation section 62 generates a dummy stimulation of a different frequency from that of the target of auditory event-related potential measurement. For example, if 500 Hz, 1000 Hz, 2000 Hz, and 4000 Hz are the frequencies which are the target of auditory event-related potential measurement, an auditory stimulation of a frequency that is outside this frequency range for measurement is generated as the dummy stimulation, e.g., 250 Hz or 8000 Hz. The sound pressure of this auditory stimulation may be set within a range of sound pressure that is the target of auditory event-related potential measurement.

At step S203, the auditory stimulation output section 61 presents the auditory stimulation generated by the dummy stimulation generation section 62 to the user 5.

With the measurement system 2 of the present embodiment, a video is presented during an auditory event-related potential measurement, and any auditory stimulation is presented at a timing which does not fall within a predetermined time range as reckoned from a timing of luminance change in the video. Moreover, when a stimulation interval from an auditory stimulation has lasted a predetermined length or longer, a dummy stimulation is presented in order to eliminate the influence of any noise component that is induced irrespective of a sensory input. As a result, a highly accurate auditory event-related potential measurement is realized, with little fluctuation in the arousal level of the user and little influence of a visual evoked potential evoked by the video.

With the auditory event-related potential measurement apparatus and auditory event-related potential measurement system according to the present disclosure, in accordance with the timings of luminance change in a video which is concurrently presented with auditory stimulations, timings of auditory stimulation presentation are scheduled so that no auditory stimulation is presented within a predetermined time range as reckoned from the timing of any luminance change. Moreover, when a stimulation interval from an auditory stimulation has lasted a predetermined length or longer, the auditory stimulation that is the first to be presented after the interval of the predetermined length or longer is excluded from the arithmetic mean, thereby excluding any noise component that is induced irrespective of the sensory input. Owing to these, a highly accurate auditory event-related potential measurement is realized while reducing a decrease in the arousal level of the user. Results of the highly accurate auditory event-related potential measurement can be used in an objective hearing evaluation of the user.

While the present disclosure has been described with respect to preferred embodiments thereof, it will be apparent to those skilled in the art that the disclosed invention may be modified in numerous ways and may assume many embodiments other than those specifically described above. Accordingly, it is intended by the appended claims to cover all modifications of the disclosure that fall within the true spirit and scope of the invention.

What is claimed is:

1. An auditory event-related potential measurement system comprising:

one or more memories; and circuitry which in operation is configured to:

presenta video to a user;

measure an electroencephalogram signal of the user;

schedule a timing of presenting an auditory stimulation so that the auditory stimulation is presented during a period in which the video is being presented to the user;

present the auditory stimulation to the user at the scheduled timing; and acquire, from the electroencephalogram signal, an event-related potential in a first time range starting from a point in time at which the auditory stimulation is presented, wherein the circuitry is configured to schedule the timing of presenting the auditory stimulation so that, when an amount of luminance change in the video exceeds a predetermined threshold value, the auditory stimulation is not presented during a second time range starting from a point in time at which the predetermined threshold value is exceeded.

2. The auditory event-related potential measurement system of claim 1, wherein in operation the circuitry is further configured to take an arithmetic mean of the acquired event-related potential, wherein, the circuitry presents a plurality of auditory stimulations including a first auditory stimulation and a second auditory stimulation, the second auditory stimulation being presented subsequent to the first auditory stimulation; and if the second auditory stimulation is presented after a time interval which is predetermined or longer from the first auditory stimulation, the circuitry takes an arithmetic mean of event-related potentials which are evoked by those auditory stimulations among the plurality of auditory stimulations excluding the second auditory stimulation.

3. The auditory event-related potential measurement system of claim 2, wherein the first auditory stimulation and the second auditory stimulation presented by the circuitry have respectively different frequencies.

4. The auditory event-related potential measurement system of claim 2, wherein, if the second auditory stimulation is presented after an interval of 2 seconds or more from the first auditory stimulation, the circuitry takes an arithmetic mean of event-related potentials which are evoked by those auditory stimulations among the plurality of auditory stimulations excluding the second auditory stimulation.

5. The auditory event-related potential measurement system of claim 2, wherein, if the second auditory stimulation is presented after an interval of 6 seconds or more from the first auditory stimulation, the circuitry takes an arithmetic mean of event-related potentials which are evoked by those auditory stimulations among the plurality of auditory stimulations excluding the second auditory stimulation.

6. The auditory event-related potential measurement system of claim 1, wherein the circuitry schedules the timing of presenting the auditory stimulation by designating as the second time range a range of not less than 50 ms and not more than 200 ms after the point in time at which the amount of luminance change exceeds the predetermined threshold value.

7. The auditory event-related potential measurement system of claim 1, wherein in operation the circuitry is further configured to retain a video content to be presented to the user, and perform a reproduction process of the retained video content, wherein the circuitry presents to the user the retained video content having been subjected to the reproduction process.

8. The auditory event-related potential measurement system of claim 7, wherein the video content does not contain audio information.

9. The auditory event-related potential measurement system of claim 7, wherein, when the video content contains any audio information, the circuitry prohibits outputting of the audio.

10. The auditory event-related potential measurement system of claim 7, wherein, the circuitry retains a plurality of types of video content; and the circuitry performs a reproduction process of a video content selected by the user from among the plurality of types of video content.

11. The auditory event-related potential measurement system of claim 1, wherein in operation the circuitry is further configured to determine which of right and left ears of the user the auditory stimulation is to be presented to and determine a frequency and a sound pressure of the auditory stimulation, and generate the auditory stimulation with characteristics so determined.

12. An auditory event-related potential measurement method comprising operating circuitry to perform the steps of:

presenting a video to a user;

measuring an electroencephalogram signal of the user;

scheduling a timing of presenting an auditory stimulation so that the auditory stimulation is presented during a period in which the video is being presented to the user;

presenting the auditory stimulation to the user at the scheduled timing; and from the electroencephalogram signal, acquiring an event-related potential in a first time range starting from a point in time at which the auditory stimulation is presented, wherein, the scheduling step includes scheduling the timing of presenting the auditory stimulation so that, when an amount of luminance change in the video exceeds a predetermined threshold value, the auditory stimulation is not presented during a second time range starting from a point in time at which the predetermined threshold value is exceeded.

13. A non-transitory computer-readable medium storing a computer program to be executed by a computer provided in an auditory event-related potential measurement apparatus of an auditory event-related potential measurement system, the computer program causing the computer to execute the steps of:

presenting a video to a user;

acquiring an electroencephalogram signal of the user;

scheduling a timing of presenting an auditory stimulation so that the auditory stimulation is presented during a period in which the video is being presented to the user;

presenting the auditory stimulation to the user at the scheduled timing; and from the electroencephalogram signal, acquiring an event-related potential in a first time range starting from a point in time at which the auditory stimulation is presented, wherein, the scheduling step includes scheduling the timing of presenting the auditory stimulation so that, when an amount of luminance change in the video exceeds a predetermined threshold value, the auditory stimulation is not presented during a second time range starting from a point in time at which the predetermined threshold value is exceeded.

14. An auditory event-related potential measurement system comprising:
one or more memories; and
circuitry which in operation is configured to:
schedule a timing of presenting an auditory stimulation so that the auditory stimulation is presented during a period in which a video is being presented to a user;
present the auditory stimulation to the user at the scheduled timing; and
acquire, from a measured electroencephalogram signal of the user, an event-related potential in a first time range starting from a point in time at which the auditory stimulation is presented, wherein
the circuitry is configured to schedule the timing of presenting the auditory stimulation so that, when an amount of luminance change in the video exceeds a predetermined threshold value, the auditory stimulation is not presented during a second time range starting from a point in time at which the predetermined threshold value is exceeded.

* * * * *